(12) United States Patent
Yamada et al.

(10) Patent No.: US 7,859,672 B2
(45) Date of Patent: Dec. 28, 2010

(54) OPTICAL ELEMENT, SENSOR DEVICE, MANUFACTURING METHOD OF OPTICAL ELEMENT, DETECTION ELEMENT, TARGET SUBSTANCE MEASURING DEVICE AND DETECTION METHOD

(75) Inventors: Tomohiro Yamada, Yokohama (JP); Yoichiro Handa, Tokyo (JP); Satoru Nishiuma, Kawasaki (JP); Ryo Kuroda, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 286 days.

(21) Appl. No.: 12/045,335

(22) Filed: Mar. 10, 2008

(65) Prior Publication Data
US 2008/0297800 A1 Dec. 4, 2008

(30) Foreign Application Priority Data
Mar. 19, 2007 (JP) .............................. 2007-070597
Mar. 19, 2007 (JP) .............................. 2007-070598

(51) Int. Cl.
*G01N 21/00* (2006.01)
(52) U.S. Cl. ....................................... 356/442; 257/226
(58) Field of Classification Search ................. 356/442; 257/226
See application file for complete search history.

(56) References Cited

U.S. PATENT DOCUMENTS

2004/0183176 A1  9/2004  Naya et al. ................... 257/680
2005/0053974 A1*  3/2005  Lakowicz et al. ............... 435/6
2007/0090411 A1  4/2007  Naya et al. .................... 257/226
2009/0153866 A1*  6/2009  Yamamichi et al. ......... 356/445
2010/0097610 A1  4/2010  Yamada et al.

FOREIGN PATENT DOCUMENTS

JP  2000-356587  12/2000
JP  2000-245639  9/2004
WO  2006/118337 A1  11/2006

OTHER PUBLICATIONS

Traci R. Jensen, et al., "Nanosphere Lithography: Effect of the External Dielectric Medium on the Surface Plasmon Resonance Spectrum of a Periodic Array of Silver Nanoparticles," J. Phys. Chem. B, 1999, vol. 103, pp. 9846-9853.
Amanda J. Haes, et al., "A Localized Surface Plasmon Resonance Biosensor: First Steps toward an Assay for Alzheimer's Disease," Nano Letters, 2004, vol. 4, No. 6, pp. 1029-1034.

* cited by examiner

*Primary Examiner*—Roy Punnoose
(74) *Attorney, Agent, or Firm*—Fitzpatrick, Cella, Harper & Scinto

(57) ABSTRACT

An optical element of the present invention includes a conductive microstructure having a conductive property, and detects an optical spectrum signal varied by the binding of measured molecules on the surface of the conductive microstructure. The optical element has a distribution in the binding capacity of the measured molecules on the surface of the conductive microstructure in the direction of the electric displacement vector generated inside the conductive microstructure. As a result, it is possible to provide an optical element capable of measuring the density at high accuracy without depending on the binding position of the measured molecules.

8 Claims, 33 Drawing Sheets

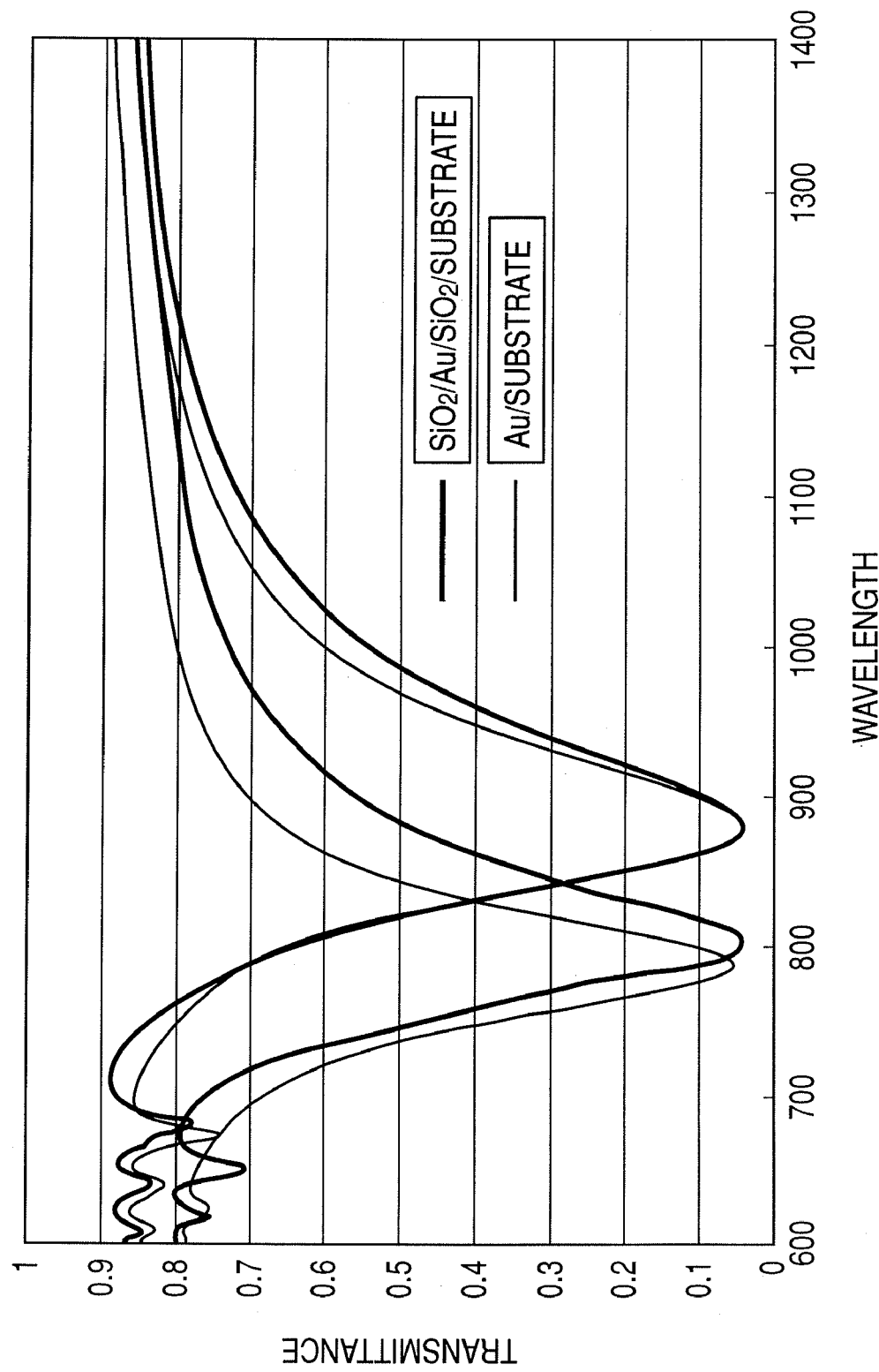

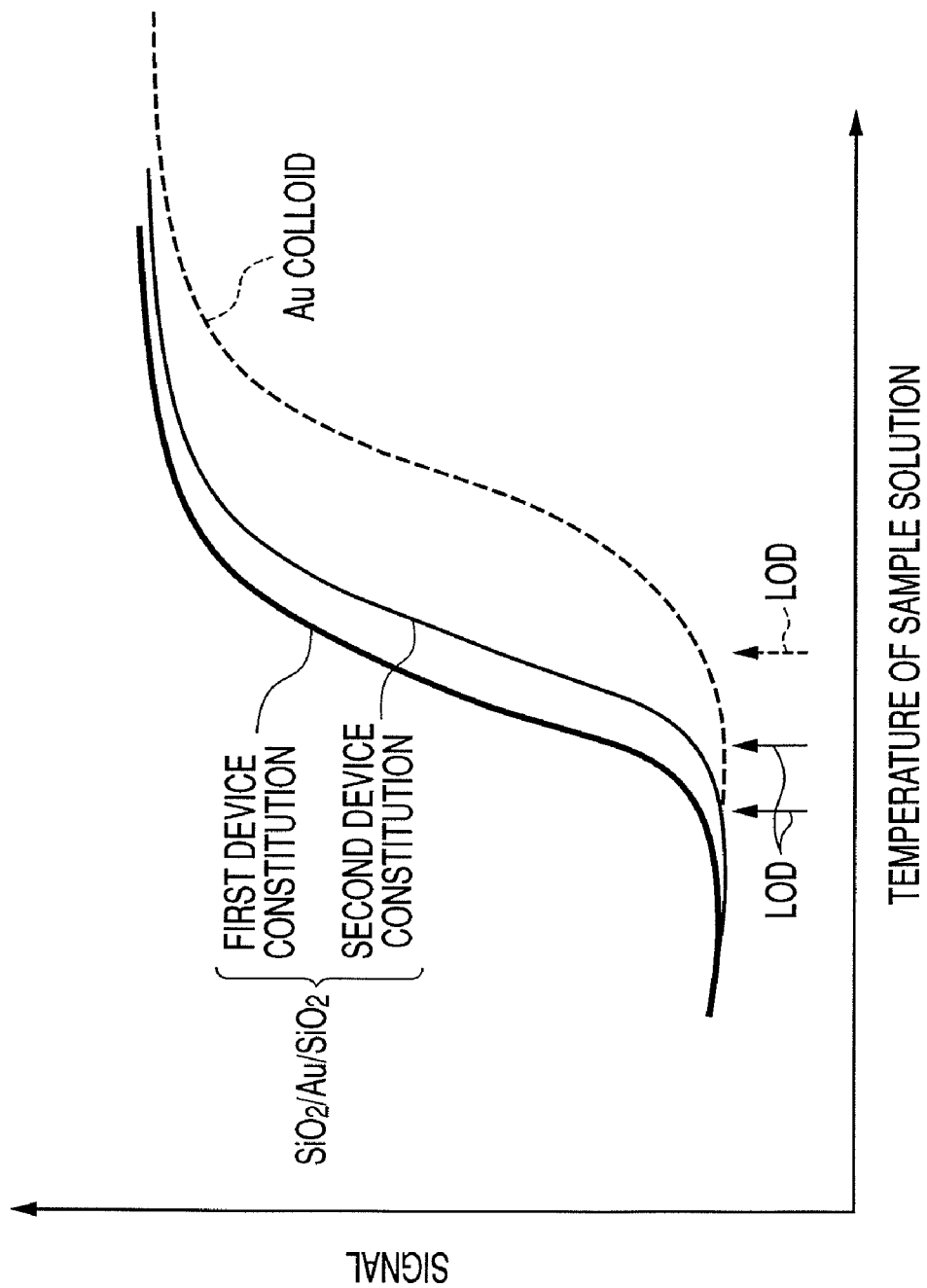

OPTICAL ELEMENT, SENSOR DEVICE, MANUFACTURING METHOD OF OPTICAL ELEMENT, DETECTION ELEMENT, TARGET SUBSTANCE MEASURING DEVICE AND DETECTION METHOD

BACKGROUND OF THE INVENTION

1. Field of the Invention

The present invention relates to optical elements, sensor devices, manufacturing method of optical elements, detection elements, target substance measuring devices and detection methods, and in particular, it relates to an optical element for detecting density of a target substance, a sensor device, and a method of manufacturing an optical element.

2. Description of the Related Art

It is known that a minute conductive structure induces Localized Surface Plasmon Resonance (hereinafter referred to as LSPR). This LSPR has its resonance condition decided by refraction index and dielectric constant of the periphery of the conductive structure. Consequently, variation of the dielectric index of the periphery of the conductive structure can be detected as variation of the resonance condition. The variation of the resonance condition can be detected by allowing the light to irradiate and transmit the conductive structure and measure the variation of the optical spectrum.

The LSPR is sensitive to the variations of the refraction index and the dielectric constant of the periphery of the conductive structure. Consequently, the LSPR can be applied to a high sensitive refraction index sensor. Further, as illustrated below, when the variation of this dielectric constant is due to biological reaction, this phenomenon is applied to a biosensor and the like to enable high sensitive sensing, and a wide range of applications can be expected in the fields of medical care, food, environment, and the like.

For example, when an antigen-antibody reaction is allowed to occur in the periphery of the conductive structure, this reaction can be detected. Richard P. Van Duyne et al., NANO LETTERS, Vol. 4, No. 6, pp. 1029-1034, 2004 discloses an example using a minute Ag thin film fine particle structure formed on a smooth substrate as the conductive structure. That is, the literature discloses the case where the periphery of this structure is adhered with an antibody, and a method of measuring an antigen density from the variation of the optical spectrum in a state in which this antibody is further bound to an antigen. Here, it is reported that a refraction index response when the ambient medium is changed is 76.4 nm/index.

In addition, a composite body of oxygen and substrate, a complementary base pairing by DNA-hybridization, and the like can be also similarly detected.

Further, Japanese Patent Application Laid Open No. 2000-356587 discloses a method of fixing Au fine particle on a glass substrate and detecting refraction index of the fine particle periphery from the spectrum of its Plasmon resonance.

Japanese Patent Application Laid Open No. 2004-245639 discloses a problem that the variation of a detection element output signal is feeble, and a detection element for solving the problem that a long period of time is required until such variation is recognized. That is, Japanese Patent Application Laid Open No. 2004-245639 discloses a detection element, in which a plurality of pores are formed on one surface, and a substrate filled with metal fine particles inside the pore is provided, and at least part of the metal fine particles is exposed outside the substrate rather than one surface.

Further, J. Phys. Chem. B 1999, 103, 9846-9853, Nanosphere Lithography: Effect of External Dielectric Medium on the Surface Plasmon Resonance Spectrum of a Periodic Array of Silver Nanoparticle discloses a technique for disposing Ag dots in side-by-side arrangement by using nanosphere lithography (lithography technique using nano beads of polyethylene) and fabricating a LSPR detection element. It is reported that the refraction index response when the ambient medium is changed is 200 nm/index.

In the case of an ordinary transit measurement including the conventional art, the variation of the dielectric constant by an antigen-antibody reaction at the conductive fine particle periphery is detected by measuring a transmission spectrum LSPR optical spectrum (before reaction) 101 and a LSPR optical spectrum (after reaction) 102 of the conductive fine particle before and after the reaction. From the variation of the resonance condition of the LSPR before and after the reaction, an antigen density is detected (FIG. 19A). The outline of the measuring system at this time, similarly to FIG. 19B, is such that a conductive fine particle 103 modified in the surface by an antibody 105 irradiates an irradiated light 107 and a transmitted light 108 to a measuring element 106 supported by a dielectric substrate 104, and measures its transmission spectrum.

Now, as described above, when the variation of the dielectric constant of a metal structure periphery is detected as the variation of an optical spectrum signal using the LSPR, in case the density of a biological substance to be measured is exceptionally low, it is quite probabilistic to which portion of the metal structure surface a measured molecule binds. Hence, the variation of the spectrum signal is different every dot, and the spectrum after being adhered with the biological substance ends up becoming broadened. As a result, a problem arises that the measuring sensitivity is lowered.

SUMMARY OF THE INVENTION

Hence, an object of the present invention is to provide an optical element capable of measuring a density at high accuracy without being affected by a binding position of the measured molecule, and a manufacturing method of a sensor device and an optical element.

To achieve the object, the optical element of the present invention includes a structure having a conductive property, and detects an optical spectrum signal varied by the binding of the measured molecules on the surface of the structure. The optical element of the present invention is characterized in that a binding capacity of the measured molecule in the surface of the structure has a distribution in the direction of electric displacement vector generated in the interior of the structure.

Further, to achieve the object, the detection element of the present invention is characterized in that a structure having a metal layer immobilized with a capture is formed on a support, and in the detection element for capturing a target substance in a liquid specimen by the capture, a surface opposite to the side facing a support of the metal layer is formed with an upper dielectric layer, and the capture is immobilized on the side face of the metal layer.

Further features of the present invention will become apparent from the following description of exemplary embodiments with reference to the attached drawings.

BRIEF DESCRIPTION OF THE DRAWINGS

FIG. 28 is a graph calculating a transmissivity for the wavelength with the detection element having the structure of the present invention and the detection element having the structure with no dielectric layer by an electromagnetic field simulation software.

FIG. 31 is a graph illustrating the analytical curve with the detection element having the structure of the present invention and the detection element having the structure with no dielectric layer.

DESCRIPTION OF THE EMBODIMENTS

The present invention relates to a technique of improving sensitivity in the measurement in the method of estimating the presence of a target substance by the variation of the optical spectrum of the conductive fine particle and the variation of other optical signals capable of inducing a LSPR.

While embodiments of the present invention will be described by using an example, this description does not impose any limit whatsoever on the present invention.

As an example, an antigen-antibody reaction is considered. Here, the target substance is taken as an antigen.

Figure 1A:
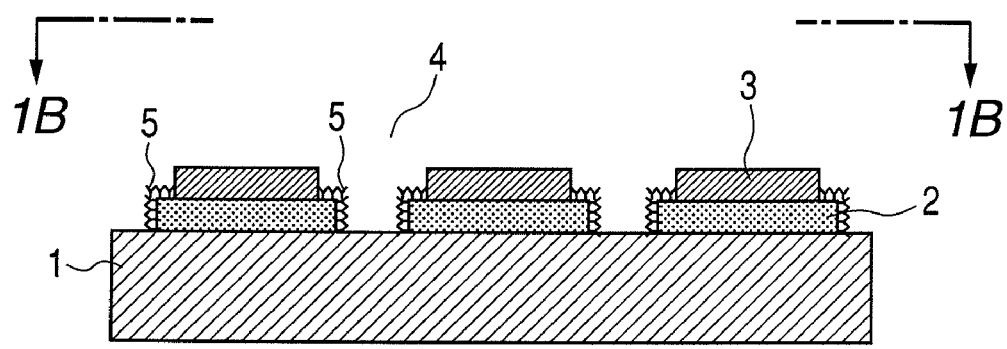
FIGS. 1A and 1B are a side view and a top plan view of an optical element of the present invention.
Figure 1B:
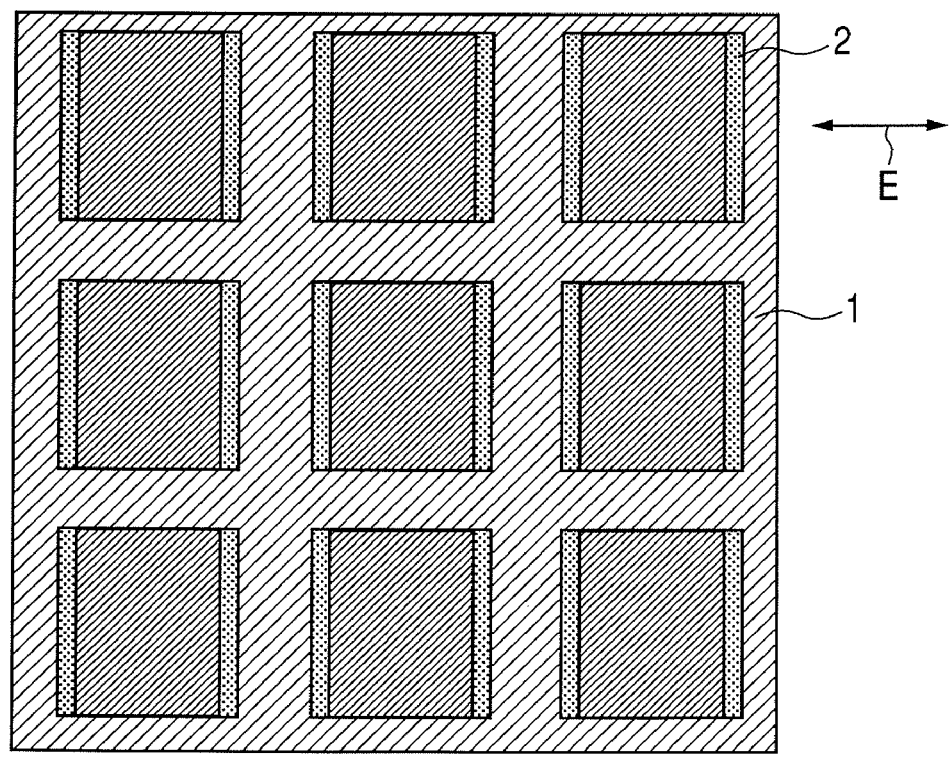

In FIGS. 1A and 1B is illustrated a side view and a top plan view of one example of an optical element of the present invention.

An optical element 4 includes a dielectric substrate 1, an conductive microstructure layer 2 formed of a structure having conductive property disposed on the dielectric substrate 1, and a dielectric layer 3 disposed on the conductive microstructure layer 2. The conductive microstructure layer 2 is formed of Au, but is not limited to this, and though a metal having little loss is preferable, the layer may be whatever metal if it is conductive. Although the dielectric substrate 1 and the dielectric layer 3 can be quartz, there is no limit imposed on the material of the dielectric substrate 1 as being the same as the material of the dielectric layer 3. However, the dielectric substrate 1 is preferable to be a substance high in a degree of transparency in the measurement wavelength used for optical measurement.

Here, a strong electric field region generated on the conductive microstructure layer 2 is considered. When a light having a certain polarization plane is irradiated on the conductive microstructure layer 2, a surface charge 12 (FIGS. 2A-2B) depending on the polarization plane and the shape of the conductive microstructure layer 2 is generated. This irradiation generates an electric displacement vector inside the conductive microstructure layer 2, and displacement current flows in that direction, and emerges as the surface charge 12 as a result. "E" refers direction of the electric field.

Figure 2A:
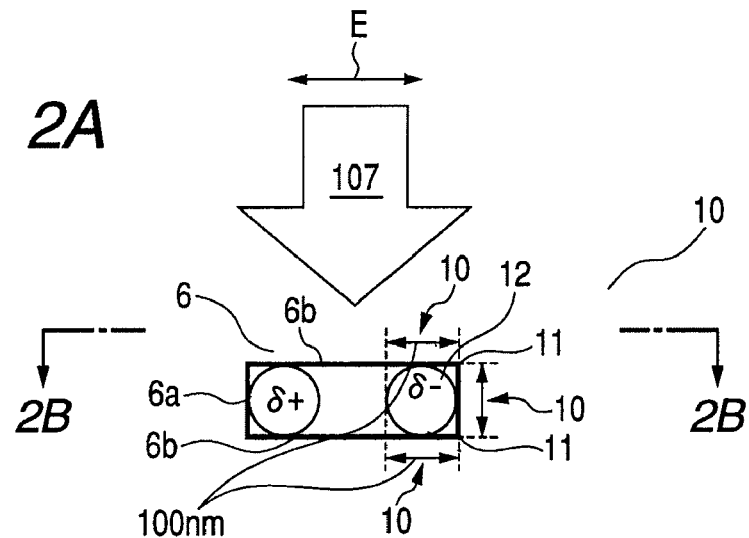
FIGS. 2A, 2B, 2C and 2D are views for explaining a distribution of a surface charge generated in a conductive microstructure.
Figure 2B:
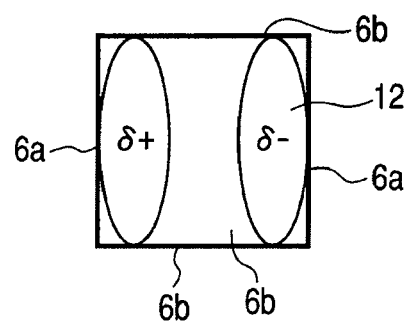
Figure 2C:
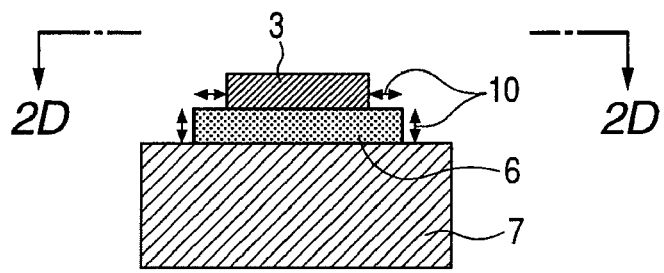
Figure 2D:
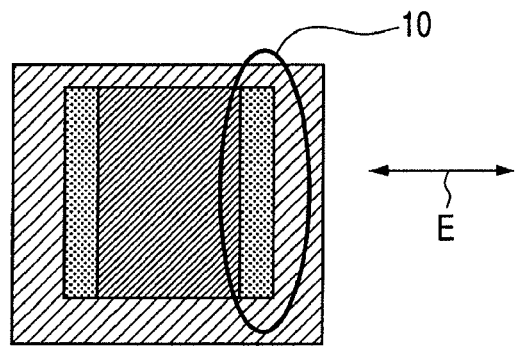

In FIGS. 2A and 2B are illustrated a distribution of the surface charge generated when a polarized light is irradiated on the square conductive microstructure. FIG. 2A is a schematic illustration illustrating a charge distribution generated inside the conductive microstructure, and FIG. 2B is a view illustrating a generated position of the strong electric field region.

Figure 5:
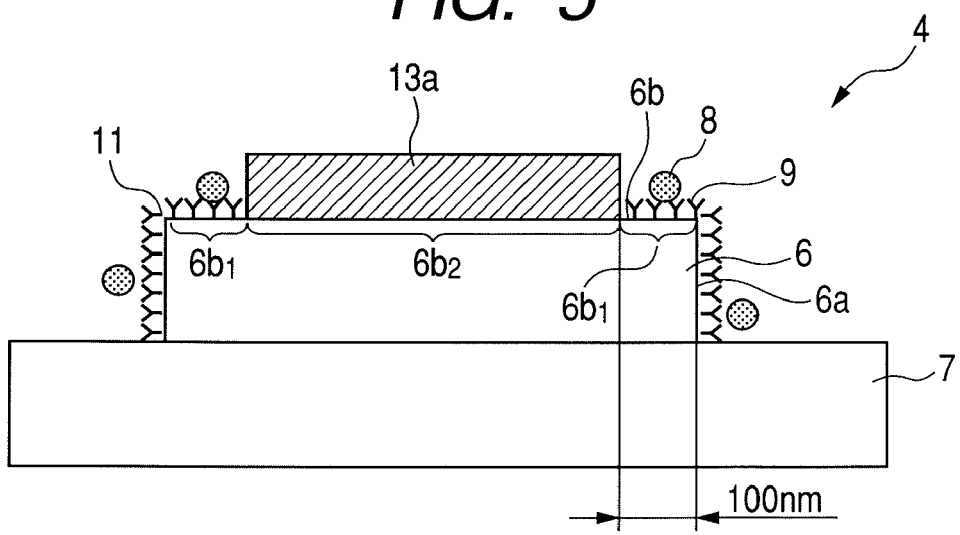
FIG. 5 is a view illustrating an example of the optical element configured to limit a region where a dielectric layer is formed on the surface of the conductive microstructure and an antigen is bound.

In this case, an end face 6a of the conductive microstructure 6 is a surface approximately orthogonal to the polarization direction, that is, a surface approximately orthogonal to the direction of the electric displacement vector. An adjacent surface 6b is a surface adjacent to the end face 6a. The adjacent surface 6b may include not only the surface irradiated with a light 107, but also the surface approximately in parallel with the direction to which the light is irradiated. A side 11 is a side contacting the end face 6a and the adjacent surface 6b. The strong electric field region 10 is generated in the end face 6a and the area $6b_1$ (see FIG. 5) within approximately 100 nm which is a predetermined distance from and the side 11 of the adjacent surface 6b.

The strong electric field region 10 is an electric field by the surface charge 12 by the localized Plasmon resonance induced in the conductive microstructure 6. Here, while the light controlling the polarization as a light from a light source has been handled, the light is not limited to this, but a non-polarized light may be irradiated. Even in this case, by that non-polarized light, the surface charge emerges as described above inside the conductive microstructure 6. Non-uniformity of such an electric charge distribution is the same as the occurrences of the electric displacement vector inside the conductive microstructure 6 in the generation direction of that non-uniformity.

Consequently, the dielectric layer 3 on the conductive microstructure 6, as illustrated in FIG. 2B, is required to be formed such that the strong electric field region 10 generated when the light from the light source is irradiated on the optical element is exposed outside. The exposed region is preferable to be aligned to all the conductive microstructures 6.

Next, an optical spectrum shift when the conductive microstructure is adhered with the biological substance is considered.

The conductive microstructure 6 is presumed to be induced with the Localized Surface Plasmon. Here, when the biological substance adheres on the conductive microstructure, its resonance condition varies, and is observed as variation of the optical spectrum.

The variation of this resonance condition differs in its degree depending on which region of the conductive microstructure 6 the biological substance adheres. That is, the variation of the optical spectrum differs depending on the adhered region.

For example, when the conductive microstructure 6 as illustrated in FIGS. 2A and 2B has a square dot shape, in case the linearly polarized light in FIGS. 2A, 2B, 2C and 2D is irradiated, the strong electric field region 10 as illustrated in FIG. 2B is generated. In this manner, when the measured molecule is adhered to the region in which the electric field strength is strong, a shift amount of the optical spectrum becomes larger as compared with the case where the measured molecule is adhered to the portion in which the electric field strength is weak.

Figure 3A:
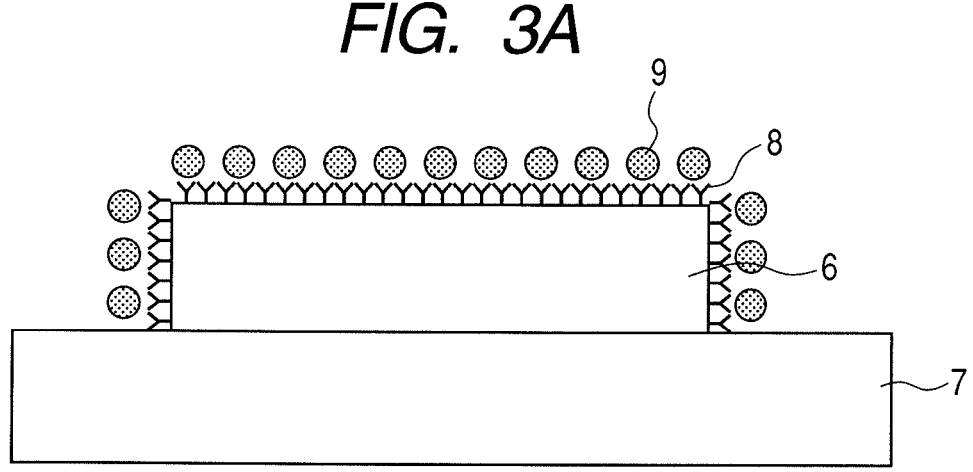
FIGS. 3A, 3B and 3C are views explaining a binding aspect of an antigen to the conductive microstructure.

Here, when the density of the antigen which is a detected substance is high, for example, when several thousands or several ten thousands order of antigens are bound for one conductive microstructure, the binding of the antigens probabilistically occurs in the surfaces of all the conductive microstructures. Hence, the aspect of the binding of the antigens can be taken approximately as the same for every conductive microstructure (FIG. 3A). In the figure, reference numbers 8 and 9 denote antibody and antigen, respectively.

Figure 3B:
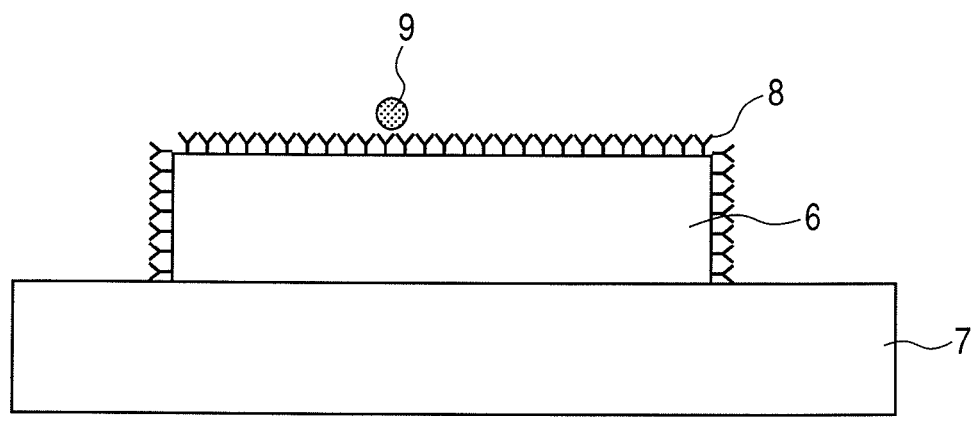
Figure 3C:
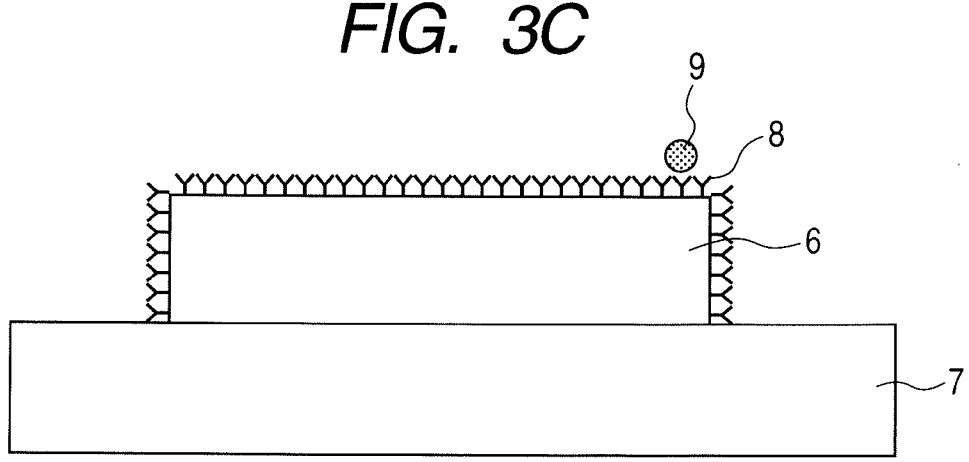

In contrast to this, for example, an extreme example where the detected molecule density is low is illustrated in FIGS. 3B and 3C. When the antigen which is the measured molecule binds only one piece to one conductive microstructure, similarly to the difference with a case 1 illustrated in FIG. 3B and a case illustrated in FIG. 3C, the region adhered with the antigen differs vastly for every conductive microstructure.

That is, the configuration illustrated in FIGS. 3A, 3B and 3C does not allow the binding capacity of the measured molecule to have a distribution on the surface of the conductive microstructure, but makes the capacity uniform despite the fact that there is the distribution in the strength of the electric field generated in the conductive microstructure. Hence, when the density of the measured substance is low, the shift amount of the optical spectrum to be detected differs depending on whether the measured molecule adheres to the portion in which the electric field strength is strong or to the portion in which the electric field strength is weak.

Figure 4A:
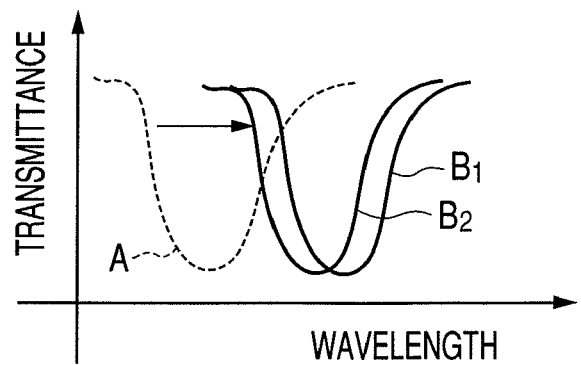
FIGS. 4A and 4B are graphs illustrating an example of the measurement result of an optical spectrum before and after an antigen-antibody reaction.

The difference of the binding regions by the case 1 and the case 2 is observed as the difference of the spectrum variation when the transmission spectrum is observed. In FIG. 4A is illustrated one example of the measured result. In the figure, the spectrum before the antigen reaction is taken as the transmission spectrum A before the reaction, and the spectrum of the case 1 is taken as a transmission spectrum B1 after a first reaction, and similarly, the case 2 is taken as a transmission spectrum B2 after a second reaction.

Figure 4B:
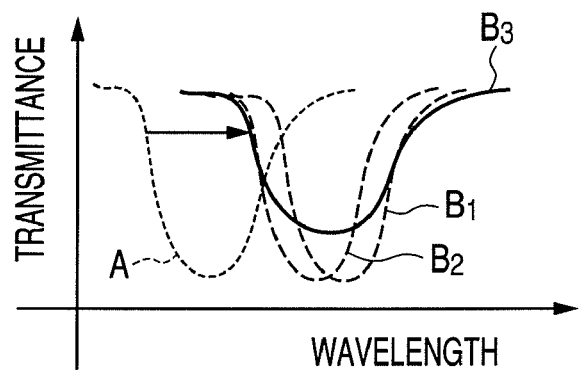

It is appreciated that the case 2, where the antigen which is the measured molecule is bound to the portion in which the electric field strength is strong, has the shift amount of the spectrum larger as compared with the case 1 where the antigen is bound to the portion in which the electric field strength is weak. When the elements of the case 1 and the case 2 are mixedly present in one measuring element, the optical spectrum after the antigen-antibody reaction becomes a total sum of various spectrums different in the shift amount, and a transmission spectrum B3 after the reaction which is a broad spectrum is observed (FIG. 4B).

In contrast to this, the optical element 4 of the present invention is configured such that the binding capacity of the measured molecule on the surface of the conductive microstructure 6 has a distribution in the direction of the electric displacement vector generated inside the conductive microstructure 6. Hereinafter, a description thereof will be made based on FIG. 5.

The conductive microstructure 6, as described above, includes the end face 6a, the adjacent surface 6b contacting the end face 6a, and the side 11 in which the end face 6a and the adjacent surface 6b are brought into contact. In the conductive microstructure 6 thus configured, the strong electric field region is generated in the end face 6a and the area $6b_1$ within an approximately 100 nm distance from the side 11 of the adjacent surface $6b$. On the other hand, the electric field generated in an area $6b_2$, which is another area other than the end face $6a$ and the area $6b_1$, is relatively weaker as compared with the electric field generated in the strong electric field region.

Hence, the optical element 4 of the present invention is configured such that the binding capacity of the measured molecule on the surface of the conductive microstructure 6 has a distribution in the direction of the electric displacement vector generated inside the conductive microstructure 6 as against the distribution of the electric field. That is, the optical element 4 is configured such that the binding capacity in the end face $6a$ and the area $6b_1$ and the binding capacity in the area $6b_2$ are different. In other words, the binding capacity in the area on the adjacent surface within a predetermined distance from the end face and the side, and the binding capacity in the area other than the end face and an area other than the area among the surface of the structure, are made different.

More specifically, the area $6b_2$ is covered with the dielectric layer $13a$ so as to suppress the binding of the measured molecules, and is configured to control the region to which the antigen binds. The optical element 4 of the present invention confines the binding of the antigen which is the measured molecule to the end face $6a$ and the area $6b_1$ in which the strong electric field region 10 is generated at the resonance time, and can prevent the antigen from binding to the area $6b_2$ of the weak electric field. That is, the optical element 4 of the present invention is limited to an adhering manner of surely generating a large variation of the optical spectrum when a biomolecule adheres to the conductive microstructure 6 by the antigen-antibody reaction.

As a result, the fluctuation of the shift amount by the difference of the binding region of the measured molecule can be suppressed, and the optical spectrum to be observed, as illustrated in FIG. 4B, can be prevented from widely spreading after the reaction. Hence, according to the optical element 4 of the present invention, even when the measured molecule density of the measured substance is low, highly accurate density measurement can be performed.

Further, the optical element 4 of the present invention may form a chemically modified portion $13b$ or a roughened concavo-convex portion $13c$ in the area $6b_2$ so as to reduce the binding capacity of the measured molecule of area $6b_2$. The manufacturing method of the optical element 4 including the chemically modified portion $13b$ or the concavo-convex portion $13c$ is as illustrated in FIGS. 6A, 6B, 6C and 6D.

Figure 6A:
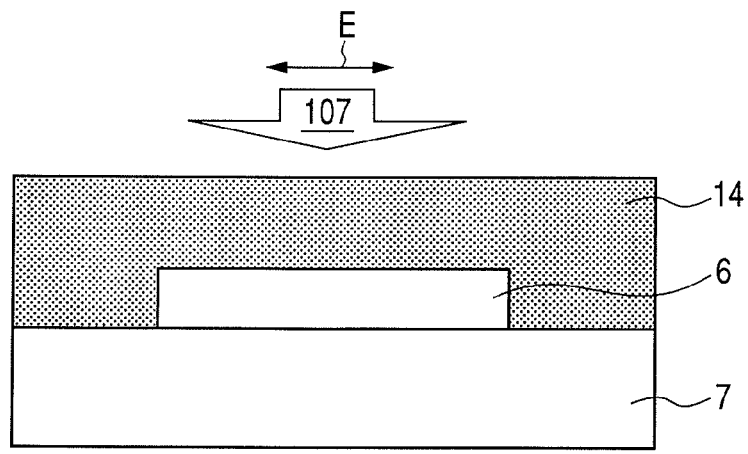
FIGS. 6A, 6B, 6C and 6D are views illustrating one example of a manufacturing method of the optical element of the present invention.
Figure 6B:
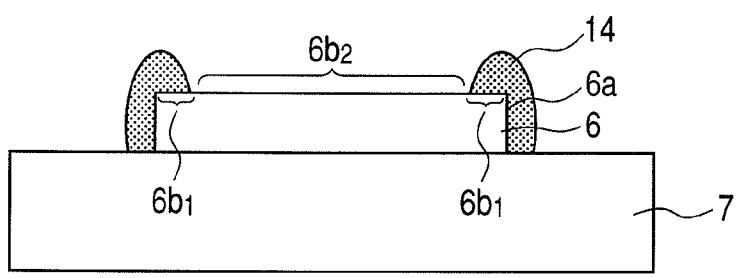

First, as illustrated in FIG. 6A, a photoresist 14 is coated so as to form a photoresist layer for a dot pattern, and an exposure light is irradiated. The electric field strength of the periphery of the conductive microstructure 6 generated by the light irradiation is strong at the end face $6a$ and the area $6b_1$. Hence, by setting an appropriate exposure time, as illustrated in FIG. 6B, the photoresist 14 of the area $6b_2$ is removed, and the photoresist 14 remains in the end face $6a$ and the area $6b_1$.

Figure 6C:
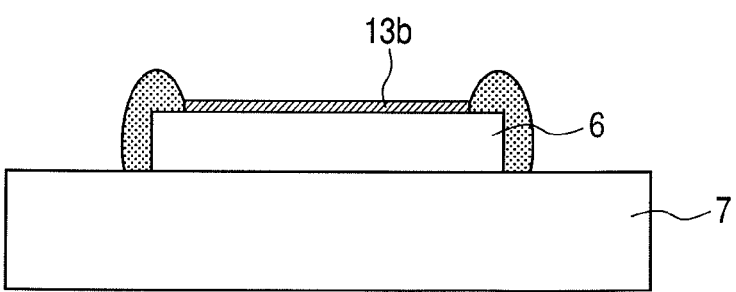
Figure 6D:
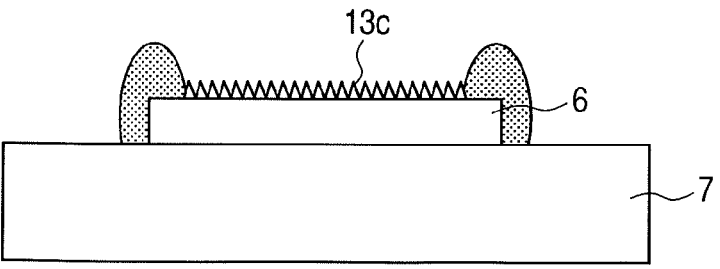

Next, the area $6b_2$ with the metal surface exposed is acted, for example, by an aqueous solution of mPEG-SH (thiol modifying polyethylene glycol) and the like, thereby to form the chemically modified portion $13b$ (FIG. 6C). As a result, the binding capacity of the measured molecule such as biomolecule and the like can be reduced.

Alternatively, the area $6b_2$ is roughened by dry etching and the like, thereby to form the concave-convex portion $13c$ and the like (FIG. 6D) so as to increase water repellent which allows the air to be contained plenty in the surface. This can reduce the binding capacity of the measured molecule of the biomolecule and the like.

After applying these processes, the photoresist 14 is removed, and the antibody is modified only in the region from which the photoresist 14 is removed. As a result, a distribution of the antibody is generated on the surface of the conductive microstructure 6 with a result that the optical element of the present invention limiting an absorption region of the antigen can be fabricated.

<Target Substance Detection Element>

Figure 20A:
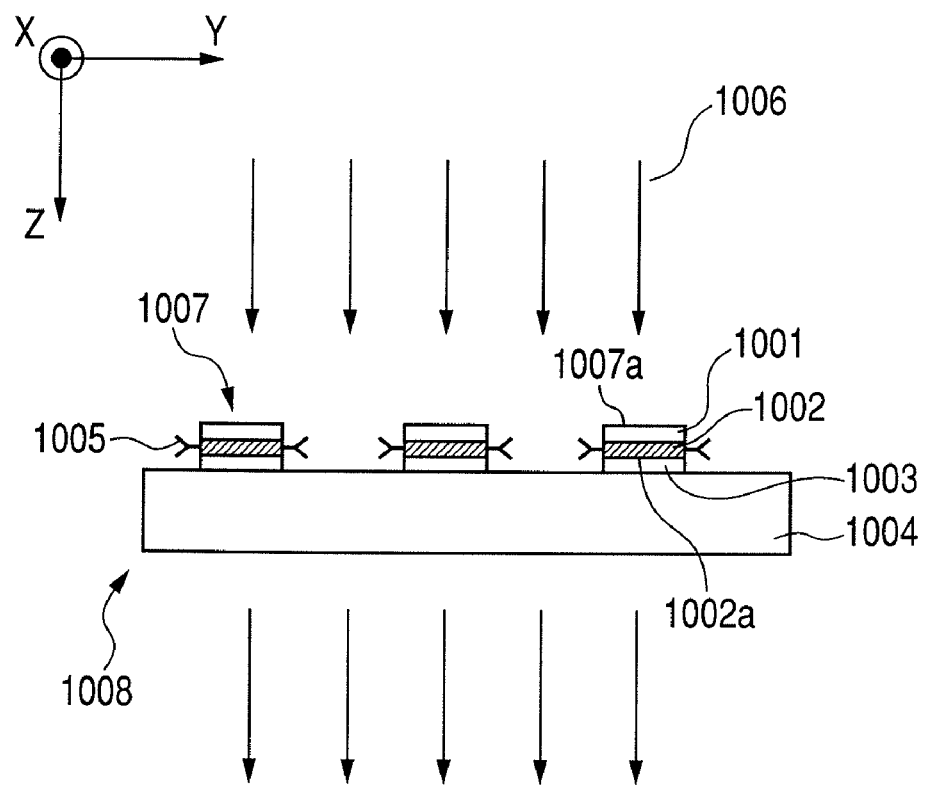
FIGS. 20A and 20B are a side view and a top plan view for explaining the outline of one example of the detection element of the present invention.
Figure 20B:
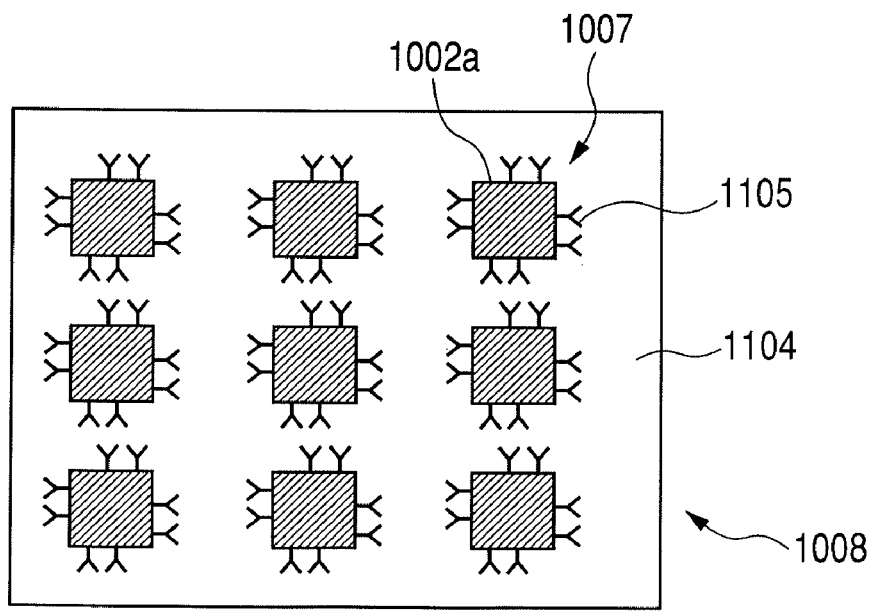

FIGS. 20A and 20B are views for explaining the outline of the detection element of the present invention, and FIG. 20A is a side view, and FIG. 20B is a top plan view.

A detection element 1008 includes a support 1004 and a structure 1007 working as the detection element disposed on the support 1004. In the description of the present specification, the detection element is sometimes referred to as the target substance detection element. The structure 1007, which is a metal nano structure, includes an upper dielectric layer 1001, a metal layer 1002, and a lower dielectric layer 1003, and only at the side face $1002a$ of the metal layer 1002, a capture 1005 is immobilized. The lower dielectric layer 1003 is formed on the support 1004, and the metal layer 1002 is formed on the lower dielectric layer 1003. That is, the lower dielectric layer 1003 is formed at the side facing the support 1004 of the metal layer 1002. The upper dielectric layer 1001 is formed on the metal layer 1002. That is, the upper dielectric layer 1001 is formed on the surface opposite to the side facing the support 1004 of the metal layer 1002.

Since the metal layer 1002 is nipped by the upper dielectric layer 1001 and the lower dielectric layer 1003 in this manner, the upper surface and the lower surface of the metal layer 1002 are not exposed, but the side face $1002a$ only is exposed. That is, since the metal layer 1002 has the side face $1002a$ only exposed, the capture 1005 is immobilized with this exposed side face $1002a$ only, and the upper surface and the lower surface of the metal layer 1002 not exposed is not immobilized with the capture 1005.

The material of the metal layer 1002 is not particularly limited if it is a metal generating the Plasmon resonance. Here, it is preferable that the metal is appropriately selected and used from among noble metals such as Au, Ag, Cu, and Pt. When the thickness of the metal layer 1002 is a thickness that allows the Plasmon to occur in the boundary face of a specimen liquid and the dielectric layer and work as the detection element, no particular limit is imposed. Here, the thickness is preferable to be in the range of 10 to 500 nm.

Further, the upper dielectric layer 1001 and the lower dielectric layer 1003 are made of organic high-polymer materials and inorganic materials.

The organic high-polymer materials can use fluorine resins, of which those having non-crystalline structures are used in terms of optical characteristics such as transparency and refraction index. They are made of, for example, either one of CYTOP (made by Asahi Glass Co., Lt.) or Teflon AF (made by Dupon Corp.) or both of CYTOP and Teflon AF.

As the inorganic material, $SiO_2$, $SiOx$, a fluorine compound ($CaF_2$, $MgF_2$, LiF, and the like) can be cited, and these materials can be appropriately selected and used.

Further, even when each of the thickness of the upper dielectric layer 1001 and the lower dielectric layer 1003 is the same or different, no particular problem is caused.

Further, a wavelength dependency of the refraction index of the upper dielectric layer 1001 and the lower dielectric layer 1003 may satisfy the following relational formula across the entire wavelength band.

$$|n_{specimen\ liquid} - n_{lower\ dielectric}| > |n_{upper\ dielectric} - n_{lower\ dielectric}|$$

$n_{specimen\ liquid}$: the diffraction index of the specimen liquid, $n_{upper\ dielectric}$: the diffraction index of the upper dielectric layer, $n_{lower\ dielectric}$: the refraction index of the lower dielectric layer, wherein n has a wavelength dependency, and the value differs depending on the light to be used. The above described relation is preferably satisfied by a visible light-infrared region (approximately 350 to 1500 nm).

By satisfying the above described relationship through the refraction indexes of the upper and lower dielectric layers, the spectrum high in Q value can be obtained regardless of the refraction index of the specimen liquid.

Further, the wavelength dependencies of the refraction index with the upper dielectric layer 1001 and the lower dielectric layer 1003 may be approximately the same. Furthermore, the wavelength dependencies of the refraction indexes of the upper dielectric layer 1001 and the support 1004 may be approximately the same.

The refraction indexes of the upper dielectric layer 1001 and the lower dielectric layer 1003 become approximately the same, so that the spectrum much higher in Q value can be obtained, and the detection sensitivity of the target substance can be improved. Further, the wavelength dependencies of the refraction indexes of the upper dielectric layer 1001 and the support 1004 are made approximately the same, so that the reflection at the substrate surface can be also reduced.

Figure 21A:
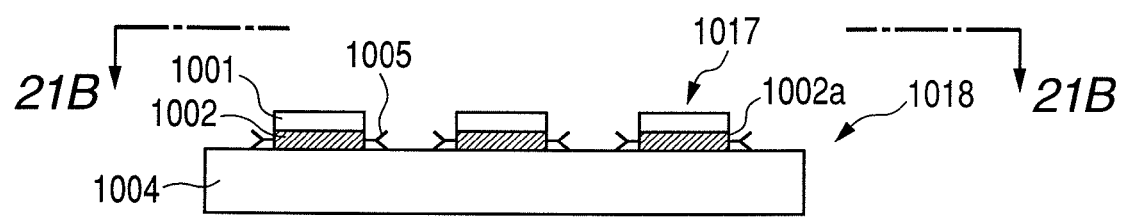
FIGS. 21A and 21B are a side view and a top plan view for explaining the outline of another example of the detection element of the present invention.
Figure 21B:
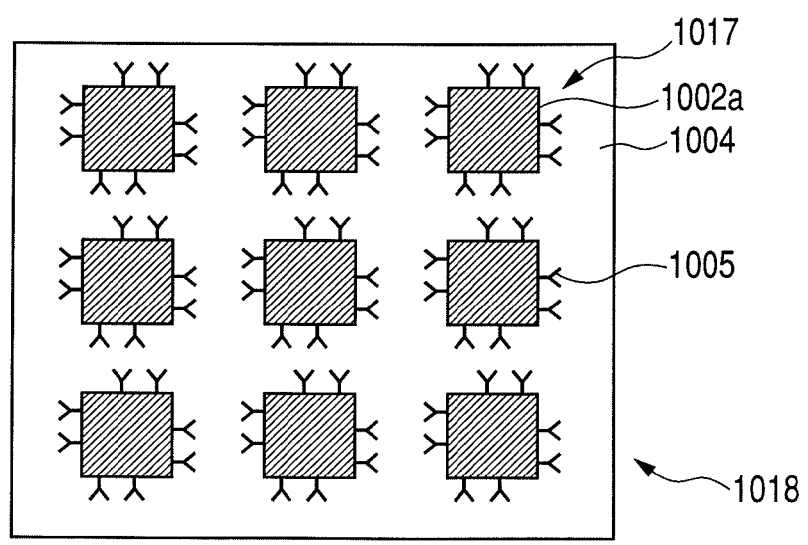

Further, the structure of the detection element of the present invention may be a two layer structure 1017 as illustrated in FIGS. 21A and 21B in addition to a three-layer structure illustrated in FIG. 20A. That is, the configuration may be such that the upper dielectric layer 1001 is formed on the surface opposite to the side facing the support 1004 of the metal layer 1002. In this case, the role of the lower dielectric layer 1003 of the structure 1007 illustrated in FIG. 20A is borne by the support 1004. The upper surface of the metal layer 1002 is covered by the upper dielectric layer 1001, and the lower surface is covered by the support 1004, so that the side face 1002a only of the metal layer 1002 is exposed.

In FIGS. 20A to 21B, although the structure of the detection element of the present invention whose planar shape is square has been illustrated, the detection element is not limited to this shape. A detection element 1028 of FIGS. 22AA and 22AB has a structure 1027 whose planar shape is rectangular. A detection element 1038 of FIGS. 22BA and 22BB has a structure 1037 whose planar shape is triangle. A detection element 1048 of FIGS. 22CA and 22CB has a structure 1047 whose planar shape is circular. Each structure of FIGS. 22AA to 22CB illustrates the three layer structure, respectively, but it may be the two layer structure as illustrated in FIGS. 21A and 21B.

Further, in FIGS. 20A to 22CB, the capture 1005 has been illustrated as equally immobilized with the side face 1002a regardless of the polarization direction of an incident light 1006, but the present invention is not limited to this. That is, as illustrated in FIGS. 23AA, 23AB, 23BA, and 23BB, the capture 1005 may be selectively immobilized with the side face vertical to the polarization direction (electric field vector). Preferably, the capture is configured to be selectively immobilized with the area where an evanescent field becomes strong (side face orthogonal to the electric field vector in FIGS. 23AA, 23AB, 23BA, and 23BB). The shape of the structure of FIGS. 23AA and 23AB shows a rectangular shape illustrated in FIGS. 22AA and 22AB, and the shape of the structure of FIGS. 23BA and 23BB shows a square shape illustrated in FIGS. 20A and 20B.

Further, the disposition of the structure on the support may be whatever disposition it is such as a square lattice disposition, a triangle lattice disposition, a hexagonal lattice disposition, a spinning object disposition, and a quasi-periodic type disposition without any particular limitation imposed. A pitch between the structures is preferably in the range of 50 to 2000 nm.

<Fabrication Process of Target Substance Detection Element>

The fabrication method of the target substance detection element may be whatever method it is if it is capable of forming a desired pattern with no particular problem caused. Even if the method is a technique by electron beam (EB) lithography, a technique using nano-imprint technology, and a technique using photolithography and X ray lithography, there is no problem caused at all. Furthermore, even if the technique is a method of spontaneous formation, there is no problem caused. Further, the method of transferring a pattern so as to form a metal-dielectric nano structure may use the etching or the structure may be formed by a lift off without any problem caused at all.

<Capture and Target Substance>

If the capture 1005 forms a specific binding pair with the target substance, there is no particular limit imposed. Here, the antibody and nucleic acid are preferably used.

If the target substance forms a specific binding pair with the capture 1005, there is no particular limit imposed. Specifically, the target substance included in the specimen liquid is classified into a non-biological material and a biological material. As those high in industrial application value as the non-biological materials, PCB class different in the chrolinc chlorine substitution number/position as environmental pollutants, similarly dioxin class different in the chrolinc chlorine substitution number/position, endocrine disruption materials such as so-called environmental hormone and the like can be cited.

The biological substances can be selected from nucleic acid, protein, sugar chain, fat, and a compound of these substances. To be more in detail, the biological substances include the biological molecules selected from nucleic acid, protein, sugar chain, and fat. Specifically, they are DNA, RNA, aptamer, gene, chromosome, cell membrane, virus, antigen, antibody, lectin, hapten, hormone, receptor, enzyme, peptide, sphingo sugar, sphingoglycolipid, and the like. If they include the substance selected from any one of those cited, whatever substance it is, the present invention can be applied to the same. Furthermore, a bacteria or a cell itself that produces the above described "biological substance" can become a target substance as the "biological substance" which is targeted by the present invention.

<Operation Principle of Detection Element>

Next, the operation principle of a chemical detection element of the present invention will be described by using FIGS. 24A, 24B and 24C.

Figure 24A:
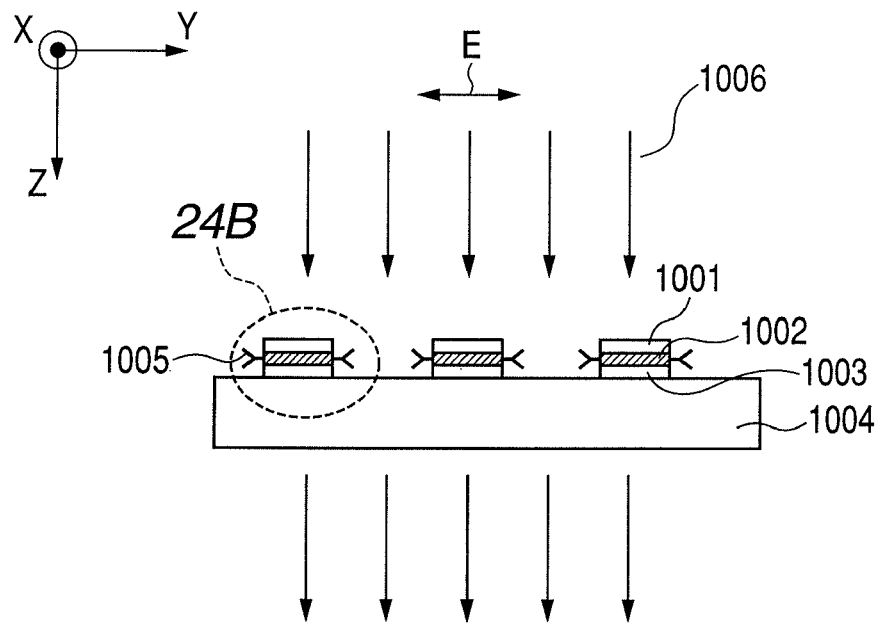
FIGS. 24A, 24B and 24C are views and a graph for explaining an operation principle of the detection element of the present invention.
Figure 24B:
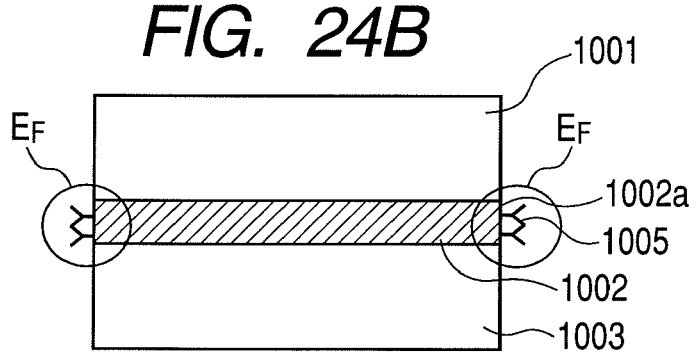

In the figure, an incident light 1006 is allowed to be incident from above to the downward direction (+z direction) (FIG. 24A). The incident light 1006 makes the coupling with a free electron inside the structure 1007, and generates an evanescent field area $E_F$ the periphery of the structure 1007 (FIG. 24B). The evanescent field area $E_F$ acutely responds to variation of the refraction index of the ambient medium.

When the capture 1005 immobilized on the side face 1002a of the metal layer 1002 of the structure 1007 is bound with the target substance in the specimen liquid, the refraction index of the periphery of the structure 1007 increases the refraction index of the water also. The resonance frequency of the Plasmon resonance varies, and a peak of absorption spectrum is shifted to the long wavelength side (FIG. 24C). By using this principle, it is possible to detect a biochemical reaction of the antigen antibody and the like.

The detection element of the present invention is immobilized with the capture 1005 at the side face 1002a only of the structure 1007 in which the evanescent field area $E_f$ occurs. Therefore, the structure 1007 and the dielectric boundary face have approximately the same resonance condition. Hence, when the incident light 1006 is irradiated, a Plasmon mode induced in the boundary face is reduced, and a line width (Q value) of the spectrum can be made narrower in band than conventionally, and the sensitivity of the detection element can be increased much more.

Heretofore, the line width (Q value) of the spectrum of the conventional detection element that immobilizes the capture 1005 also on the upper surface of the structure in which the evanescent field area $E_f$ does not occur has been broad. In contrast to this, in the case of the present invention, as compared with the conventional configuration, a narrow band spectrum can be obtained, and it is, therefore, possible to perform a sensing more sensitive than the conventional detection element.

<Target Substance Measuring Device>

(Measuring Device Using Reaction Well)

Figure 25A:
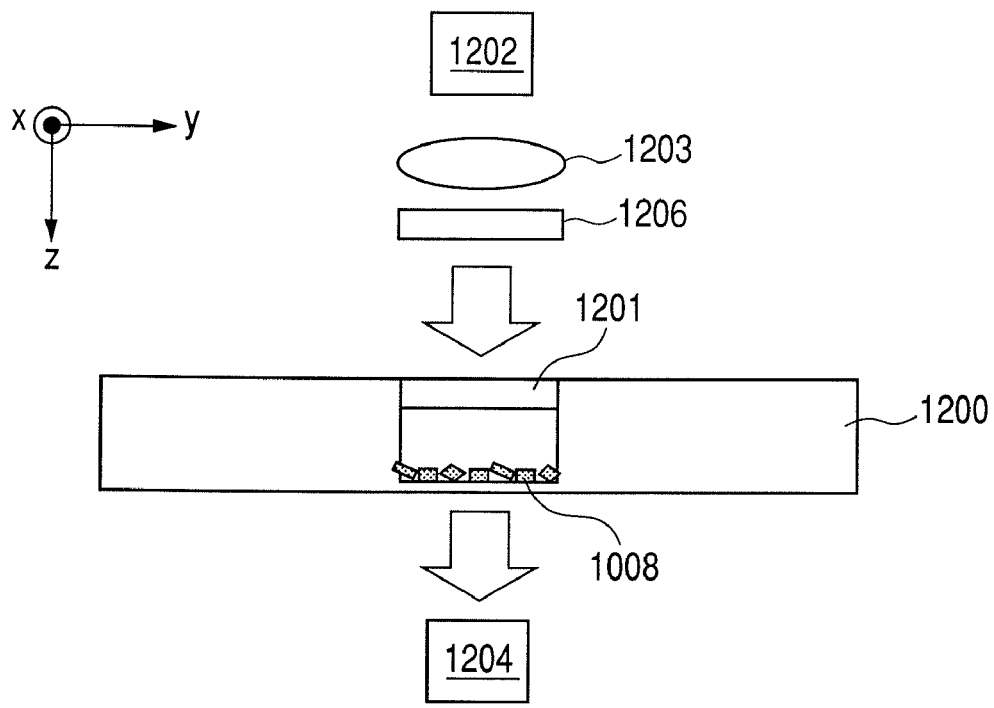
FIGS. 25A and 25B are schematic diagrams of one example of the measuring device including the detection element of the present invention.
Figure 25B:
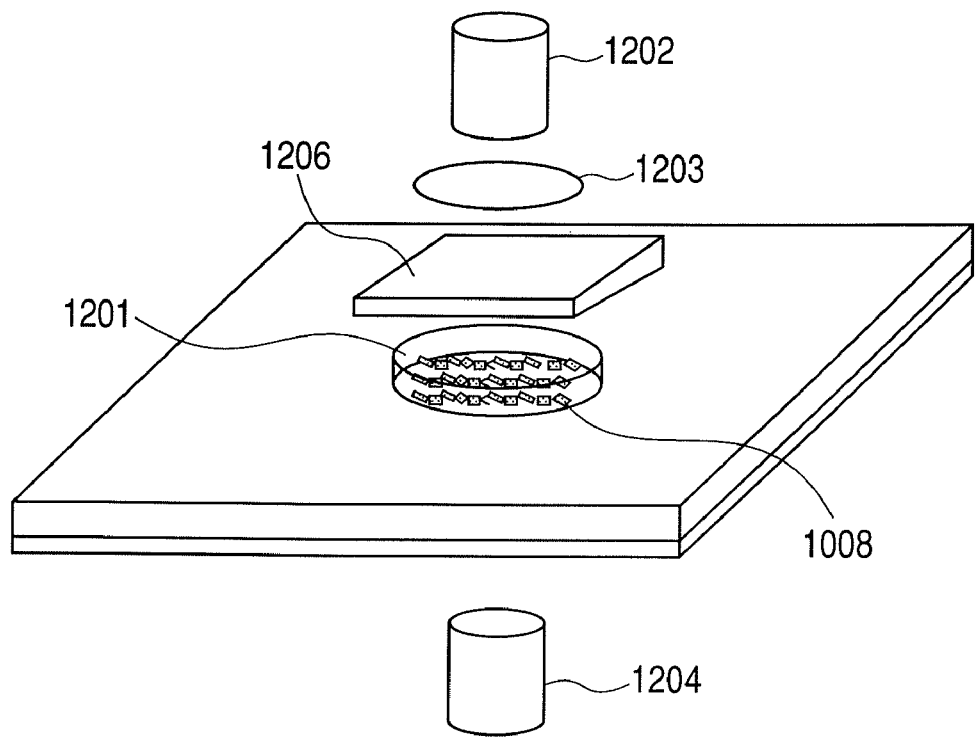

The measuring device of the present invention for measuring the target substance will be described with reference to FIGS. 25A and 25B. FIG. 25A is a cross sectional view of the measuring device of the present invention, and FIG. 25B is a perspective view thereof.

The measuring device of the present invention includes a light source 1202, an object lens 1203, a polarizing element 1206, a substrate 1200 formed with a reaction well 1201, the detection element of the present invention disposed inside the reaction well 1201, and a light receiving unit 1204.

The light source 1202 has no limit imposed if it is a stable light source. In the present invention, a halogen lamp is preferably used. The object lens 1203 has no problem at all if it can approximately collimate the incident light from the light source 1202. Here, the object lens having no chromatic aberration is more preferably used. The polarizing unit 1206 has any particular limit imposed if it can create a polarizing light. Here, a polarizer for creating a polarized light in a y direction is preferably used. The light receiving unit 1204 is preferably a spectroscopic measuring device having wavelength resolution of approximately 1 nm. In the present invention, a multi-channel detector and a spectral photometer are preferably used.

The reaction well 1201 preferably uses a material formed of the material having little non-specific adsorption of the target substance (or the member of the well is coated by a non-specific adsorption prevention layer). Inside the reaction well 1201, the detection element 1008 of the present invention is disposed. The detection element inside the reaction well 1201 is not limited to the detection element 1008, but may be detection elements 1018, 1028, 1038, and 1048.

(Measuring Device using Micro-Flow Path)

Figure 26A:
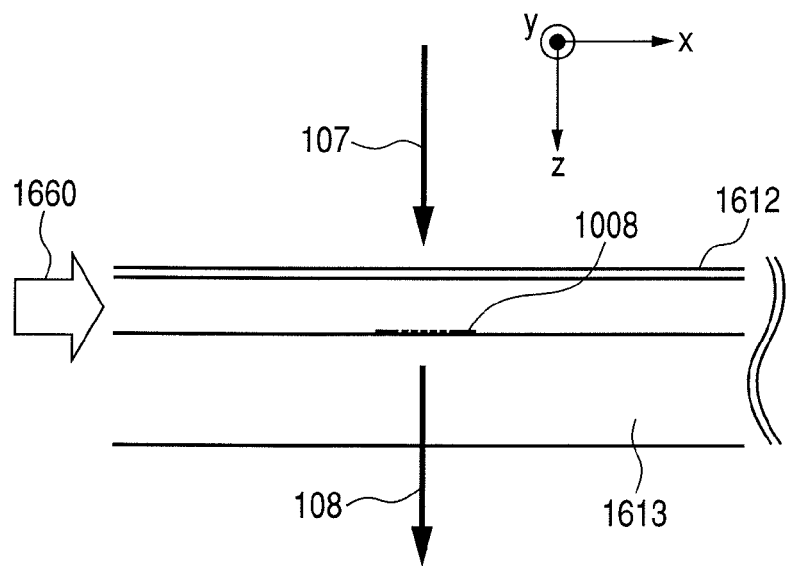
FIGS. 26A and 26B are schematic diagrams of one example of the measurement device using a micro flow path including the detection element of the present invention.
Figure 26B:
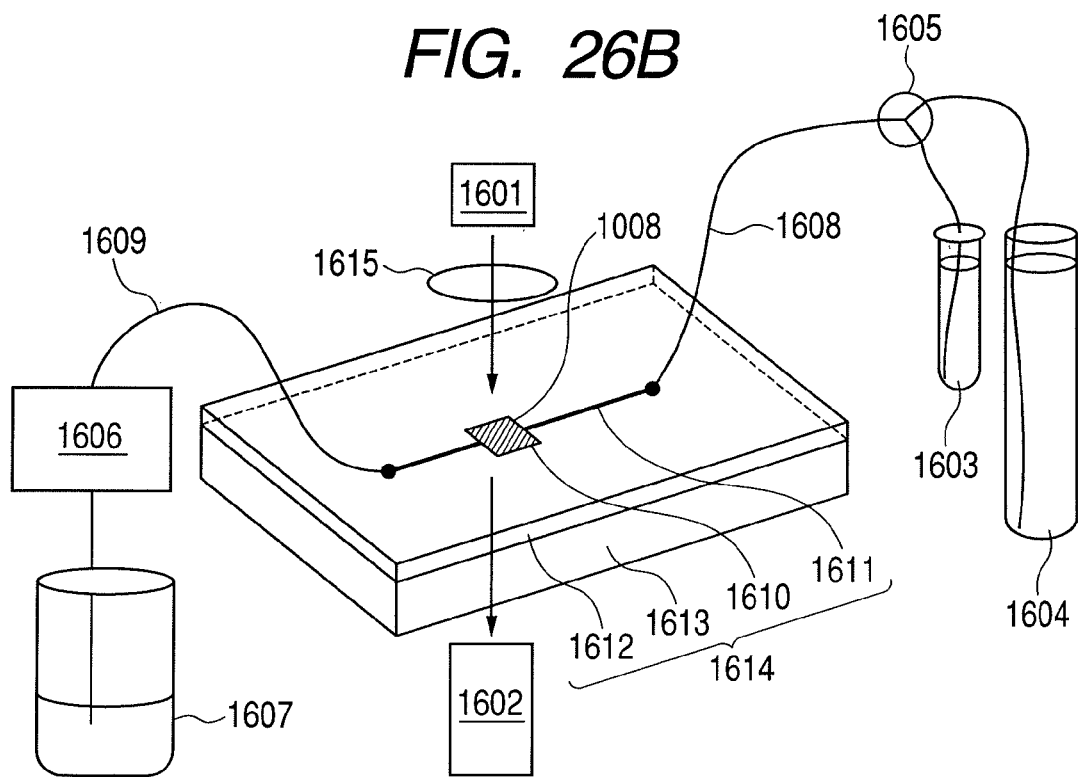

The measuring device using a micro-flow path of the present invention for measuring the target substance will be described with reference to FIGS. 26A and 26B. FIG. 26A is a partial cross sectional view of the measuring device of the present invention, and FIG. 26B is an oblique view thereof. An arrow 1660 indicates a direction into which the specimen liquid flows.

The measuring device using the micro-flow path of the present invention is formed of an optical measuring system and a liquid flow path system.

The optical measuring system includes a light source 1601, an object lens 1615, and a light receiving unit 1602. The liquid flow path system includes a liquid supply system, a target substance detection chip 1614, and a waste liquid recovery system.

The light source 1601 has no particular limit imposed if it is a stable light source. In the present invention, a halogen lamp is preferably used. The light receiving unit 1602 is preferably a spectroscopic measuring device having a wavelength resolution of approximately 1 nm. In the present invention, a multi-channel detector and a spectral photometer are preferably used.

The liquid supply system includes a specimen reservoir 1603 and a cleaning liquid reservoir 1604, which are connected to one end of a flow path 1611 of a target substance detection chip 1614 through a flow path switching valve 1605 and a liquid feeding tube 1608.

The target substance detection chip 1614 includes a substrate 1613, a flow path 1611, and a cover 1612 formed with the reaction well 1610.

Inside the reaction well 1610, the detection element 1008 of the present invention is disposed. The detection element inside the reaction well 1610 is not limited to the detection element 1008, but may be detection elements 1018, 1028, 1038, and 1048.

The specimen reservoir 1603 may prepare a reservoir formed of a material having little non-specific adsorption of the target substance or a reservoir into a chip. In the present invention, an Eppendorf tube covered with a non-specific adsorption prevention coating is preferably used.

The cleaning liquid reservoir 1604 has no particular limit imposed. Here, a glass of biochemical examination grade or plastic tube is preferably used.

The flow path switching valve 1605 has no particular limit imposed if it can switch over the tube of the liquid. In the present invention, a three-way valve is preferably used.

The waste liquid recovery system includes the liquid feeding unit 1606 and a waste liquid tank 1607, and is connected to the other end side of the flow path 1611 of the target substance detection chip 1614 through a waste liquid tube 1609.

The liquid feeding unit 1606 can appropriately select and use a syringe pump, a tube pump, a diaphragm pump, and the like.

The waste liquid tank 1607 uses a syringe itself as a waste liquid tank when the syringe pump is used for the pump. When the tube pump and the diaphragm pump are used, a beaker and a bottle can be used as the waste liquid tank. Further, when the specimen is available little, it is not turned into the waste liquid, but the specimen may be circulated by using the flow path and the tube for circulation.

The liquid feeding and the waste liquid tubes 1608 and 1609 are preferably the tubes of the material having as little adsorption as possible of the target substance.

EMBODIMENTS

Hereinafter, the present invention will be described by the embodiments, but under no circumstances, these embodiments limit the scope of the present invention.

First Embodiment

Figure 7A:
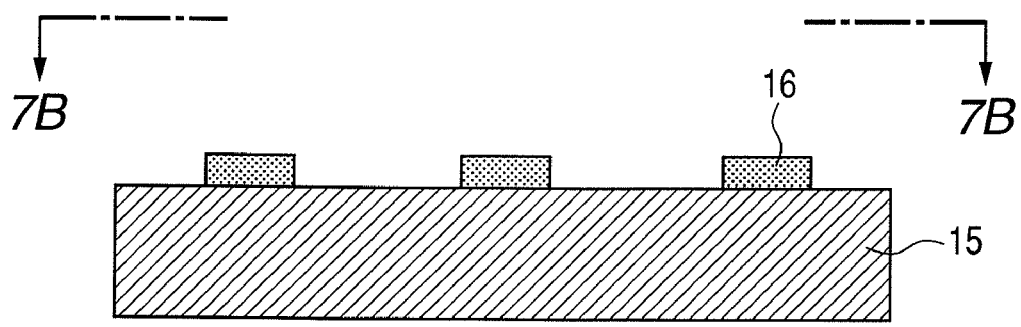
FIGS. 7A and 7B are schematic diagrams of the optical element in a preliminary step of forming the dielectric layer of a first embodiment of the present invention.
Figure 7B:
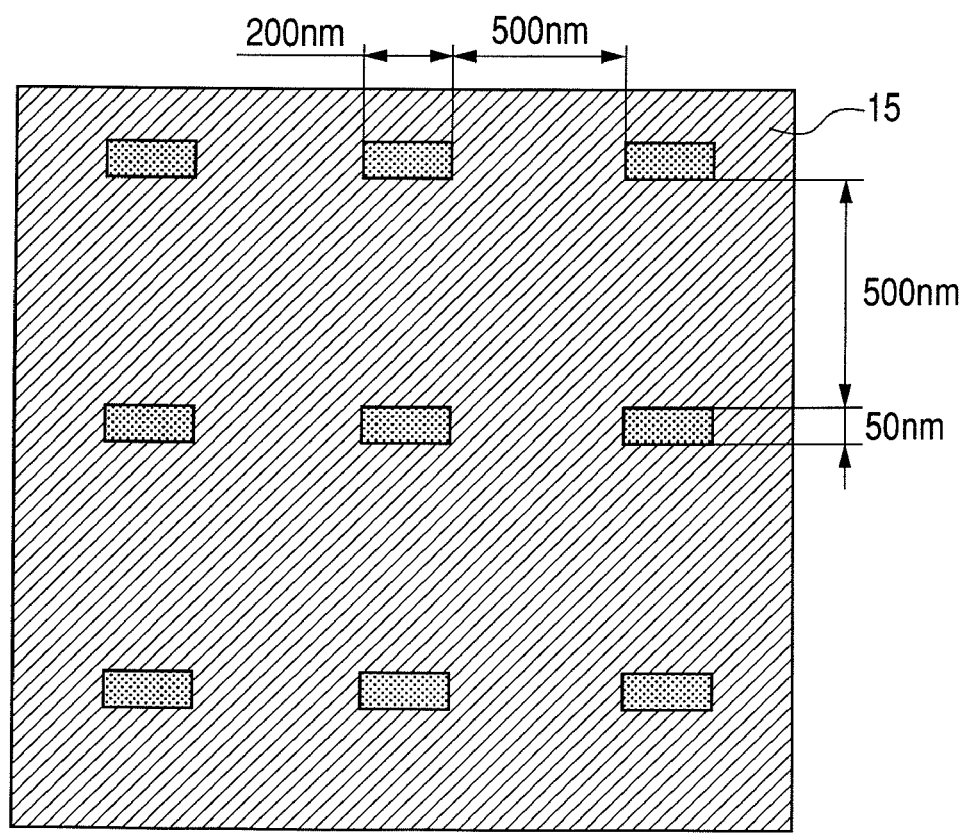
Figure 8A:
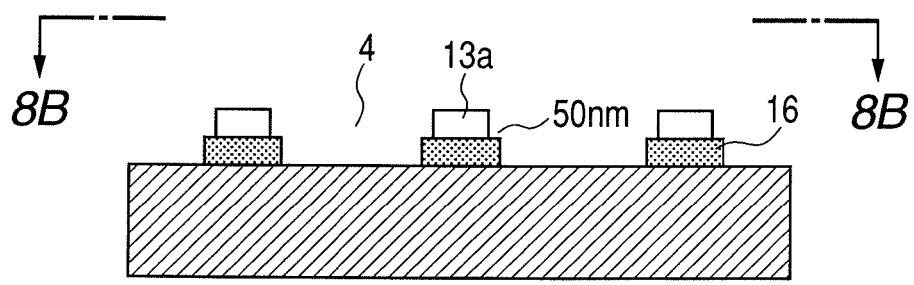
FIGS. 8A, 8B and 8C are schematic diagrams of the optical element in state in which the dielectric layer is formed and the surface is modified by an antibody.
Figure 8B:
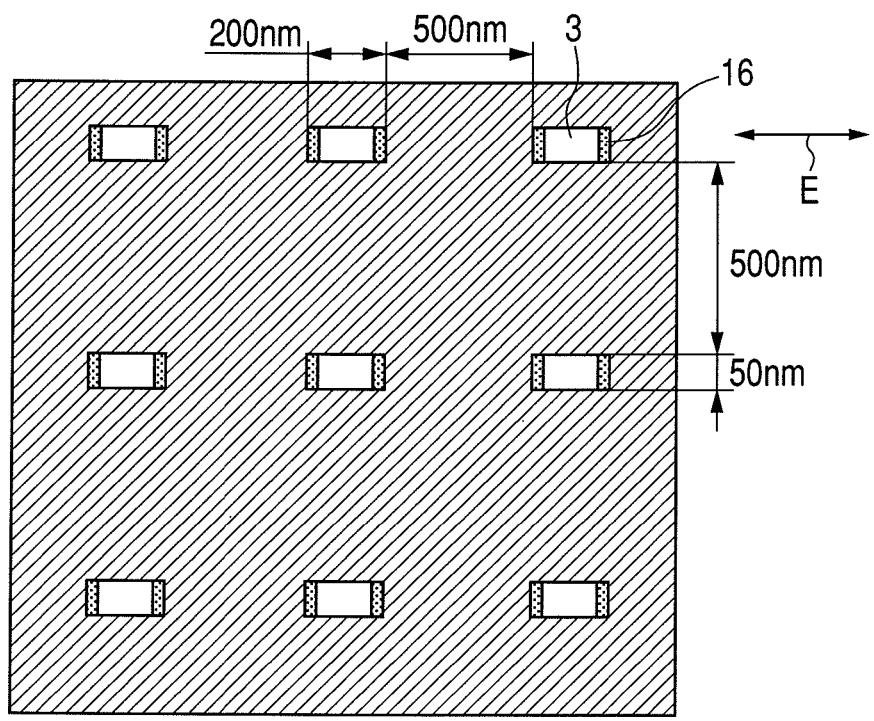
Figure 8C:
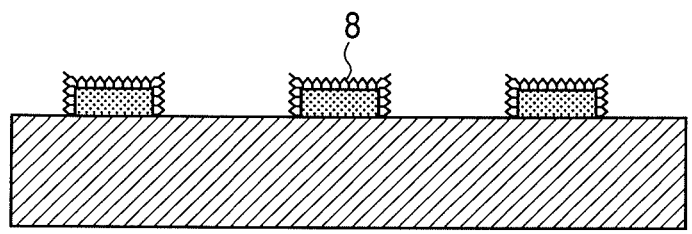

In FIGS. 7A and 7B are illustrated a schematic diagram of an optical element of the present embodiment at the preliminary stage of forming a dielectric layer. Further, in FIG. 8A is illustrated a state of forming a dielectric layer, and in FIG. 8B is illustrated a schematic diagram of an optical element in a state in which the surface is decorated with an antibody.

Hereinafter, the manufacturing method of the optical element of the present invention will be described.

First, a conductive layer is formed on a support 15 serving as a substrate. The conductive layer is prepared in advance, which is formed into a rectangular conductive fine particle 16 of approximately 200 nm×50 nm on a side as illustrated in FIG. 7B, and is disposed in a lattice shape spaced at the intervals of approximately 500 nm.

The support 15 is a quartz substrate of approximately 525 μm in thickness, and the conductive fine particle 16 on the support 15 is an Au thin film of approximately 20 nm in thickness. However, the thickness of the conductive fine particle 16 is not limited to this. In the present embodiment, the material of the conductive fine particle 16 is not exclusively limited to Au, but is preferably a material capable of generating Plasmon resonance. As the material of the conductive fine particle 16, a material including particularly the one selected from the group of silver, copper, platinum, and aluminum is preferable. Thus, as the material of the conductive fine particle 16, a metal having little dielectric loss is preferable, and other conductive substance such as a semiconductor is also preferable. Further, the support 15 is not limited to quartz, but a material high in transmissivity for the wavelength band for measuring the optical spectrum is preferable. The thickness of the support 15 also is not limited to this.

Next, $SiO_2$ is deposited approximately 20 nm in thickness by using a sputtering device. Further, after coating a resist on the film, the film is subjected to patterning by using an electron beam drawing device. By a dry etching process, the dielectric layer 13a is subjected to patterning (FIG. 8A). At this time, the dielectric layer 13a is kept fabricated at approximately 50 nm inside from the end face of the conductive fine particle 16.

Here, the dielectric layer is not limited to $SiO_2$. Further, the deposition method is not limited to sputtering, but CVD and like may be used.

After going through the above described processes, the optical element 4 is constructed.

At this time, the measuring light for this optical element 4 is a linearly polarized light, and has a polarized plane illustrated in FIG. 8A (in the direction of an arrow E).

Next, the surface of the conductive fine particle 16 is modified by the antibody.

For example, an anti-AFP (α-fetoprotein) antibody is immobilized on the Au surface of the conductive fine particle 16 as an antibody. In this case, the ethanol solution of 11-Mercaptoundecanoic acid having a thiol group is dripped by a spotter and the like, so that a carbolic group is exposed on the fine particle surface. Here, N-Hydroxysulfosuccinimide aqueous solution and 1-Ethyl-3-[3-dimenthylamino]proplyl carbodiimide hydrochloride aqueous solution are similarly dripped into the reaction area by the spotter and the like. As a result, a succinimide group is exposed on the fine particle surface. Here, streptoamidin is reacted, so as to modify the fine particle surface by streptoamidin. This fine particle is immobilized with the anti-AFP antibody biotinized. As a result, the conductive fine particle 16 is put into a state modified by the antibody 8 similarly to FIG. 8B.

Next, the antigen-antibody reaction and the optical spectrum measurement of a conductive microstructure element 55a formed with the dielectric layer 13a as described above will be described.

Figure 9A:
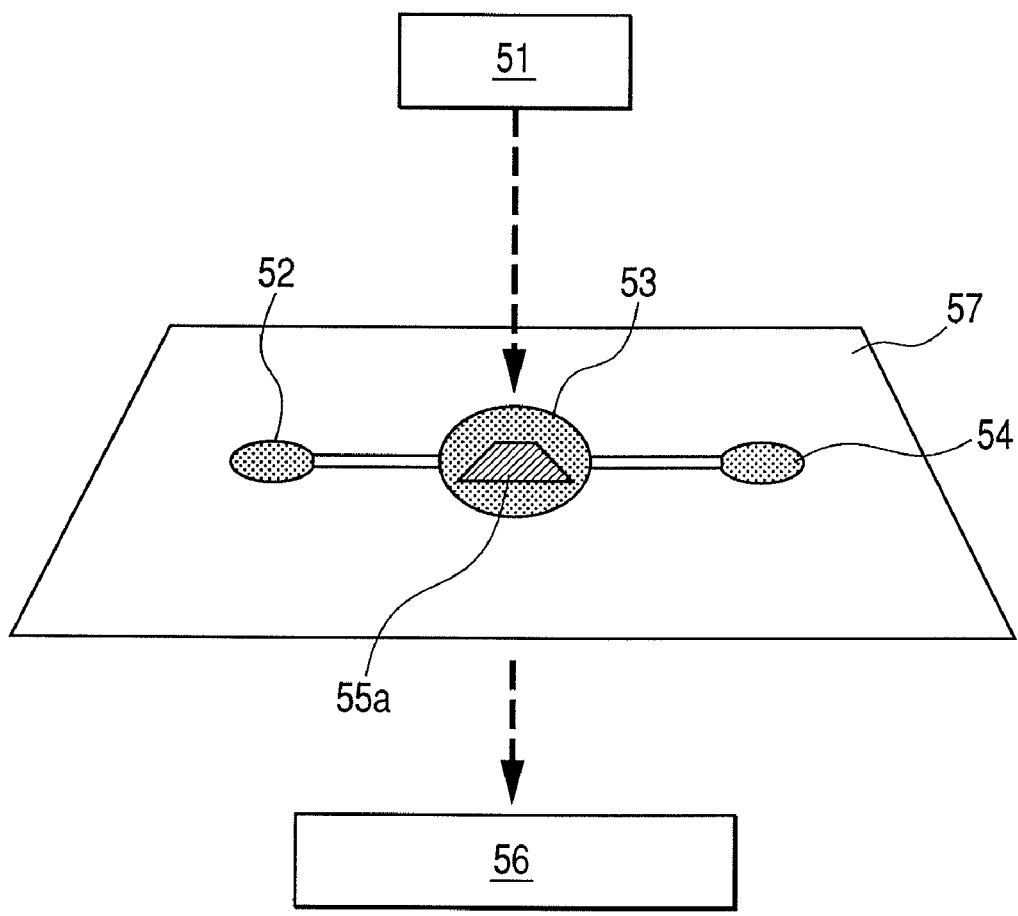
FIGS. 9A and 9B are a schematic diagram of a device performing the measurement of the antigen-antibody reaction and the optical spectrum, and a graph illustrating the measurement result of the optical spectrum.

The antigen-antibody reaction and the optical spectrum measurement are performed by the configuration using a measurement substrate 57 as illustrated in FIG. 9A.

First, the specimen including the AFP is injected from an injection port 52, and at the reaction well 53, the AFP is trapped on the conductive microstructure element 55a. After that, a specimen is discharged from a discharge port 54, and a phosphate buffer solution is injected from the injection port 52, and the interior of the reaction well 53 is cleansed. Finally, the phosphate buffer solution is filled.

Next, the optical spectrum of the conductive microstructure element 55a, the light from the light source 51 is introduced to the conductive microstructure element 55a and a scattered light from the conductive microstructure element 55a is measured by the spectroscopic measuring device 56.

Figure 9B:
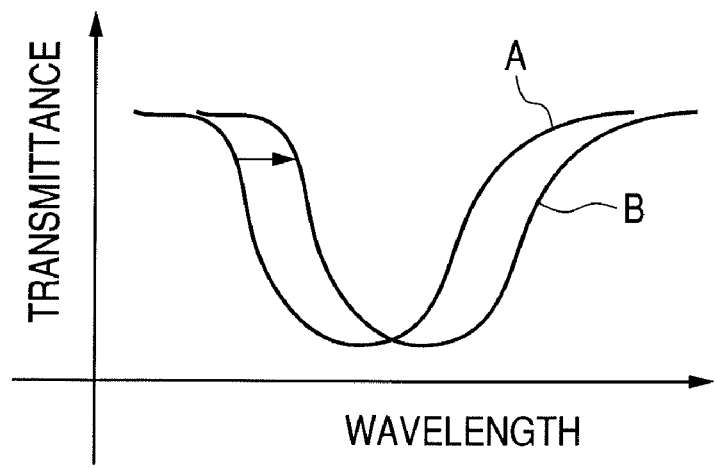

The optical spectrum is compared with the optical spectrum A before the reaction of the antigen antibody and the optical spectrum B after the reaction (FIG. 9B), the shift amount of the peak by the localized Plasmon resonance is determined, and from this shift amount, the density of the target substance is detected.

At this time, by using the AFP solution whose density is known in advance, the relationship between the signal value and the density is determined, so that the density of the measured specimen can be determined.

The optical element of the present invention is configured to form the dielectric layer 13a on the surface of the conductive microstructure and limit the region bound with the antigen. As a result, the fluctuation of the shift amount due to the difference in the bound region is suppressed, and a wide spreading of the observed optical spectrum after the reaction is suppressed. Hence, according to the optical element of the present invention, a highly accurate density measurement can be performed.

In the present embodiment, while the structure of the conductive fine particle has been taken as a rectangular thin film, it is not limited to this, but may be a structure inducing the LSPR. Further, the light source for irradiating is not limited to the linearly polarized light, but may be a partially polarized light or non-polarized light.

Second Embodiment

Figure 10A:
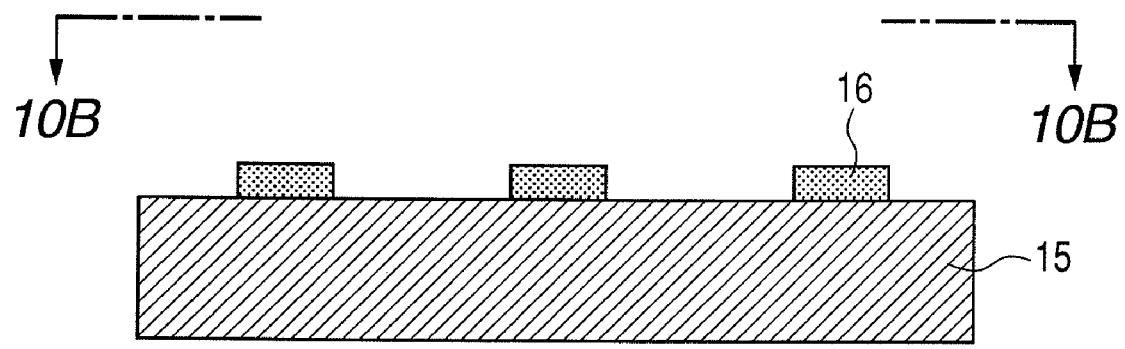
FIGS. 10A and 10B are schematic diagrams of the optical element of the embodiment in the preliminary step of forming a chemically modified portion of the second embodiment of a present invention.
Figure 10B:
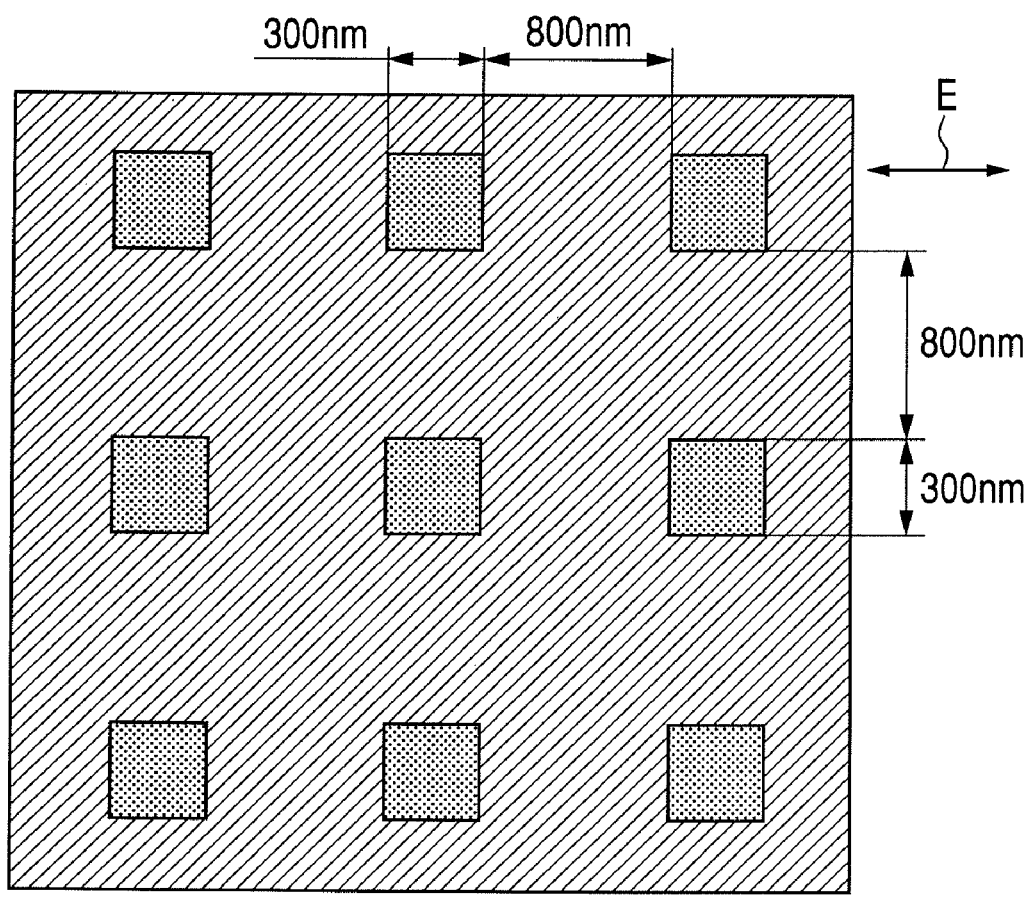
Figure 11A:
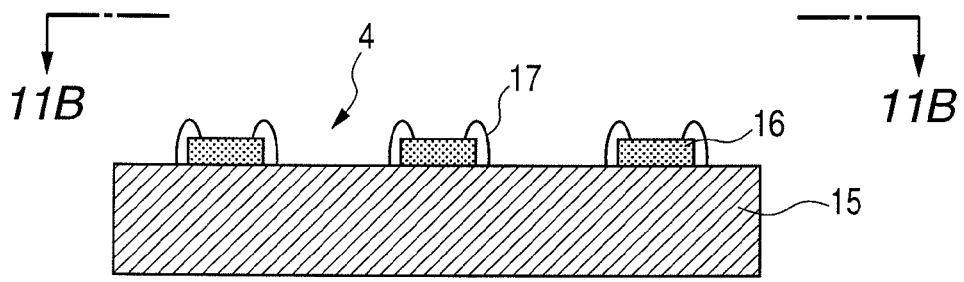
FIGS. 11A, 11B and 11C are schematic diagrams of the optical element in a state in which a resist layer is formed and the chemically modified portion is formed.
Figure 11B:
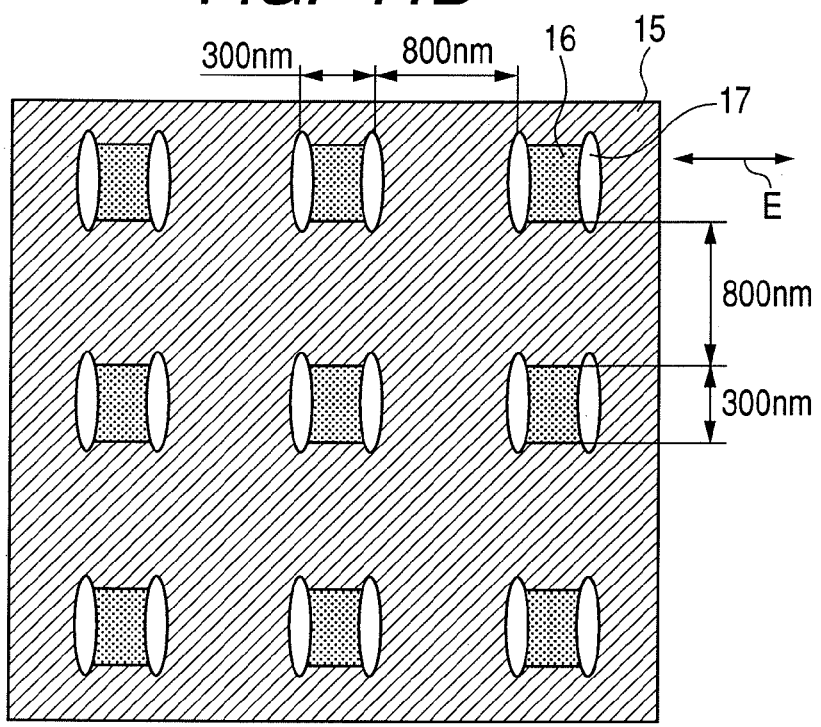
Figure 12A:
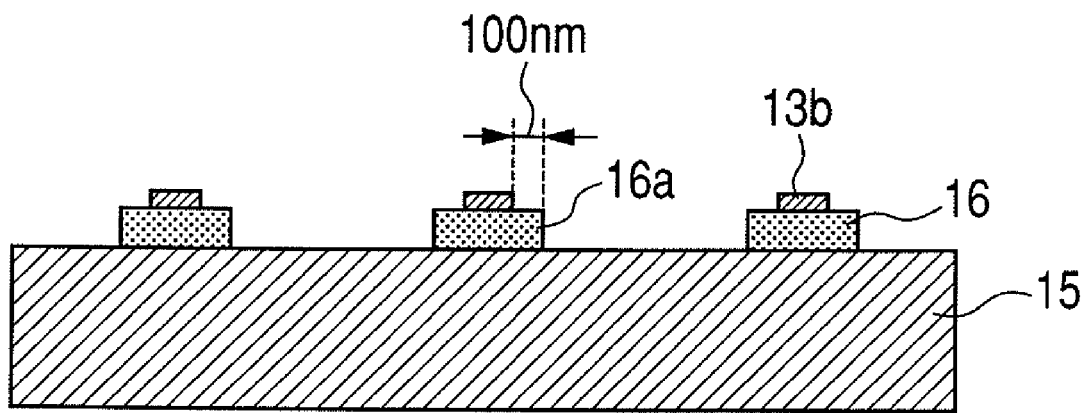
FIGS. 12A and 12B are schematic diagrams of the optical element in a state in which a resist layer is removed and the surface is decorated by an antibody.
Figure 12B:
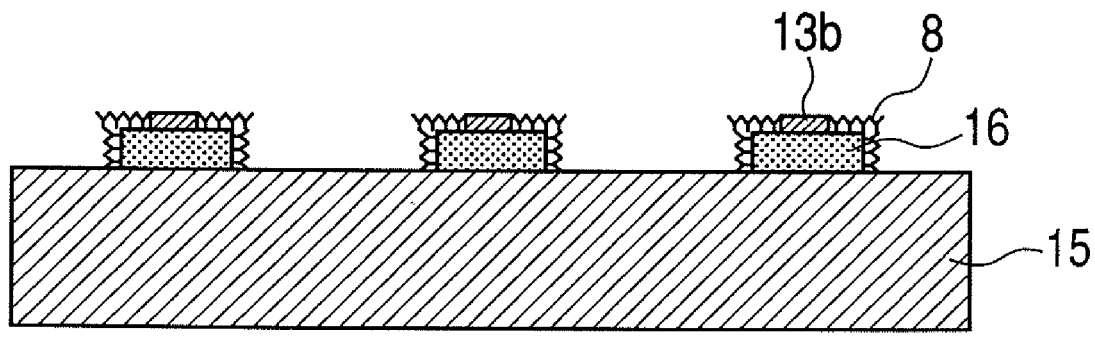

In FIGS. 10A and 10B are illustrated a schematic diagram of an optical element of the present embodiment at the preliminary stage of forming a chemically modified portion. Further, in FIG. 11A is illustrated a state of forming a resist layer, in FIG. 11B is illustrated a state of forming a chemically modified portion, in FIG. 12A is illustrated a state of removing a resist layer, and in FIG. 12B is illustrated a schematic diagram of an optical element in a state of decorating the surface by an antibody, respectively. Hereinafter, the manufacturing method of the optical element of the present embodiment will be described.

First, a conductive layer is formed on a support 15 serving as a substrate. The conductive layer is prepared in advance, which is formed into a square shape of 300 nm on a side as illustrated in FIG. 10B, and is disposed in a square lattice shape spaced at the intervals of approximately 800 nm.

The support 15 is a quartz substrate of approximately 525 μm in thickness, and a conductive fine particle 16 on the support 15 is an Au thin film of approximately 20 nm in thickness. However, the thickness of the conductive fine particle 16 is not limited to this. In the present embodiment, the material of the conductive fine particle 16 is not exclusively limited to Au, but a material capable of generating Plasmon resonance is preferable. The material of the conductive fine particle 16 is preferably a metal having little dielectric loss particularly such as Ag, Pt, Cu, and Al, and other conductive substance such as a semiconductor may be also preferable. Further, the support 15 is not limited to quartz, but a substance high in transmissivity for the wavelength band for measuring the optical spectrum is preferable. The thickness of the support 15 also is not limited to this.

Next, by using a photolithography, a resist pattern is formed. After having coated a negative type photoresist, an exposure light is irradiated and a patterning is performed. At this time, an exposure is made in an exposure time in which a strong electric field area only in the vicinity of the conductive fine particle 16 is exposed so as to form a latent image. This latent image is developed, thereby to form a patterned resist layer 17 (FIGS. 11A and 11B).

Figure 11C:
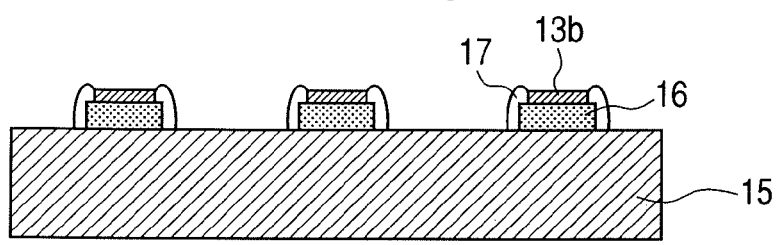

Further, an aqueous solution of thiol modification polyethylene glycol is acted on the surface of the conductive fine particle 16, thereby to form a chemically modified portion 13b (FIG. 11C). The aqueous solution acted here is not limited to thiol modification polyethylene glycol aqueous solution, but may be a substance in which, as a result of the action, the antigen and the antibody become hard to bind to the acted surface.

At this time, the measuring light for this optical element 4 is a linearly polarized light, and has a polarized surface (in the direction to an arrow E) illustrated in FIG. 11B.

Next, the surface of the conductive fine particle 16 is modified by the antibody.

First, by using acetone and the like, the resist layer 17 only is put into a separated state (FIG. 12A). At this time, the chemically modified portion 13b is disposed approximately 100 nm inside from the end face 16a of the conductive fine particle 16.

Next, an anti-AFP (α-fetoprotein) antibody is immobilized with the Au surface of the conductive fine particle 16 as an antibody. In this case, the ethanol solution of 11-Mercaptoundecanoic acid having a thiol group is dripped by a spotter and the like, so that a carbolic group is exposed on the particle surface. Here, N-Hydroxysulfosuccinimide aqueous solution and 1-Ethyl-3-[3-dimenthylamino]proplyl carbodiimide hydrochloride aqueous solution are similarly dripped into the reaction area by the spotter and the like. As a result, a succinimide group is exposed on the fine particle surface. Here, streptoamidin is reacted, so as to modify the fine particle surface by streptoamidin. This fine particle is immobilized with the anti-AFP antibody biotinized. As a result, the conductive fine particle 16 is put into a state modified by the antibody 8 similarly to FIG. 12B.

Next, the antigen-antibody reaction and the optical spectrum measurement of a conductive microstructure element 55b formed with the chemically modified portion 13b as described above will be described.

Figure 13A:
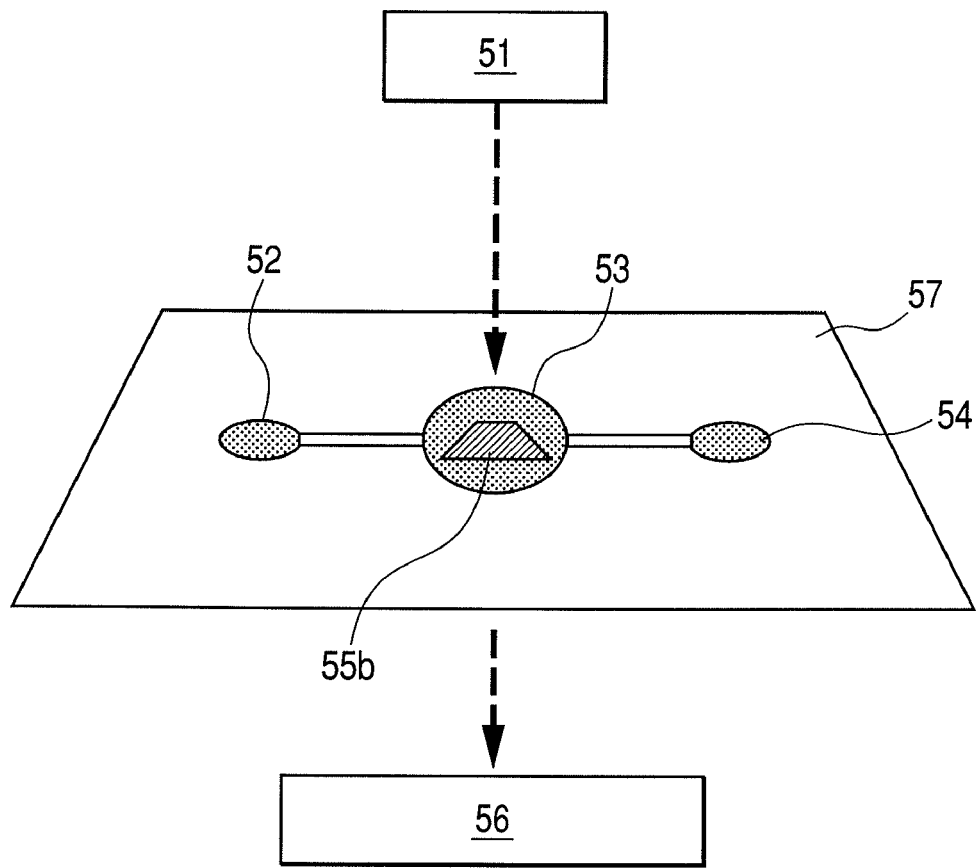
FIGS. 13A and 13B are a schematic diagram of the device performing the measurement of the antigen-antibody reaction and the optical spectrum, and a graph illustrating the measurement result of the optical spectrum.

The antigen-antibody reaction and the optical spectrum measurement are performed by the configuration using a measurement substrate 57 as illustrated in FIG. 13A.

First, the specimen including the AFP is injected from an injection port 52, and at the reaction well 53, the AFP is trapped on the conductive microstructure element 55b. After that, the specimen is discharged from a discharge port 54, and a phosphate buffer solution is injected from the injection port 52, and the interior of the reaction well 53 is cleansed. Finally, the phosphate buffer solution is filled.

Next, the optical spectrum of the conductive microstructure element 55b, the light from the light source 51 is introduced to the conductive microstructure element 55b and a scattered light from the conductive microstructure element 55b is measured by the spectroscopic measuring device 56.

Figure 13B:
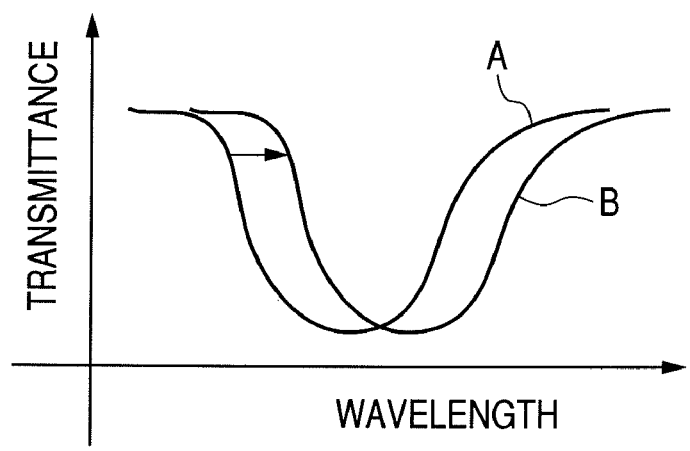

The optical spectrum is compared with the optical spectrum A before the reaction of the antigen antibody and the optical spectrum B after the reaction (FIG. 13B), the shift amount of the peak by the localized Plasmon resonance is determined, and from this shift amount, the density of the target substance is detected.

At this time, by using the AFP solution whose density is known in advance, the relationship between the signal value and the density is determined, so that the density of the measured specimen can be determined.

The optical element of the present invention is configured to form the chemically modified portion 13b on the surface of the conductive microstructure and restrict the region bound with the antigen. As a result, the fluctuation of the shift amount due to the difference in the bound region is suppressed, and a wide spreading of the observed optical spectrum after the reaction is suppressed. Hence, according to the optical element of the present invention, highly accurate density measurement can be performed.

In the present embodiment, while the structure of the conductive fine particle has been taken as a rectangular thin film, it is not limited to this, but may be a structure inducing the LSPR. Further, the light source for irradiating is not limited to the linearly polarized light, but may be a partially polarized light or non-polarized light.

Third Embodiment

Figure 14A:
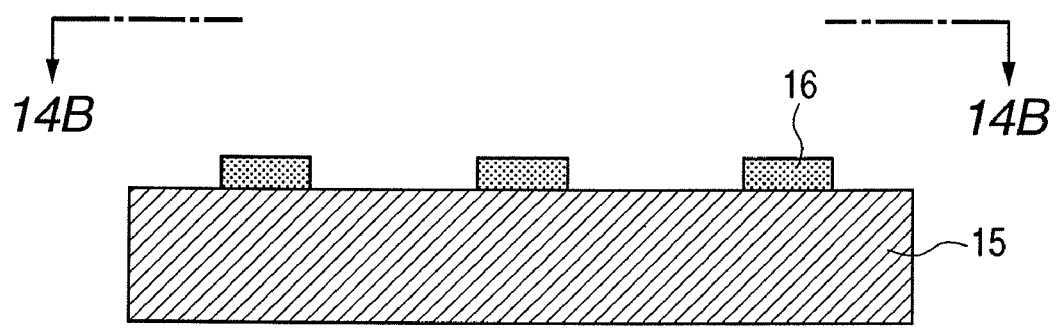
FIGS. 14A and 14B are schematic diagrams of the optical element in the preliminary step of forming a concavo-convex portion of a third embodiment of the present invention.
Figure 14B:
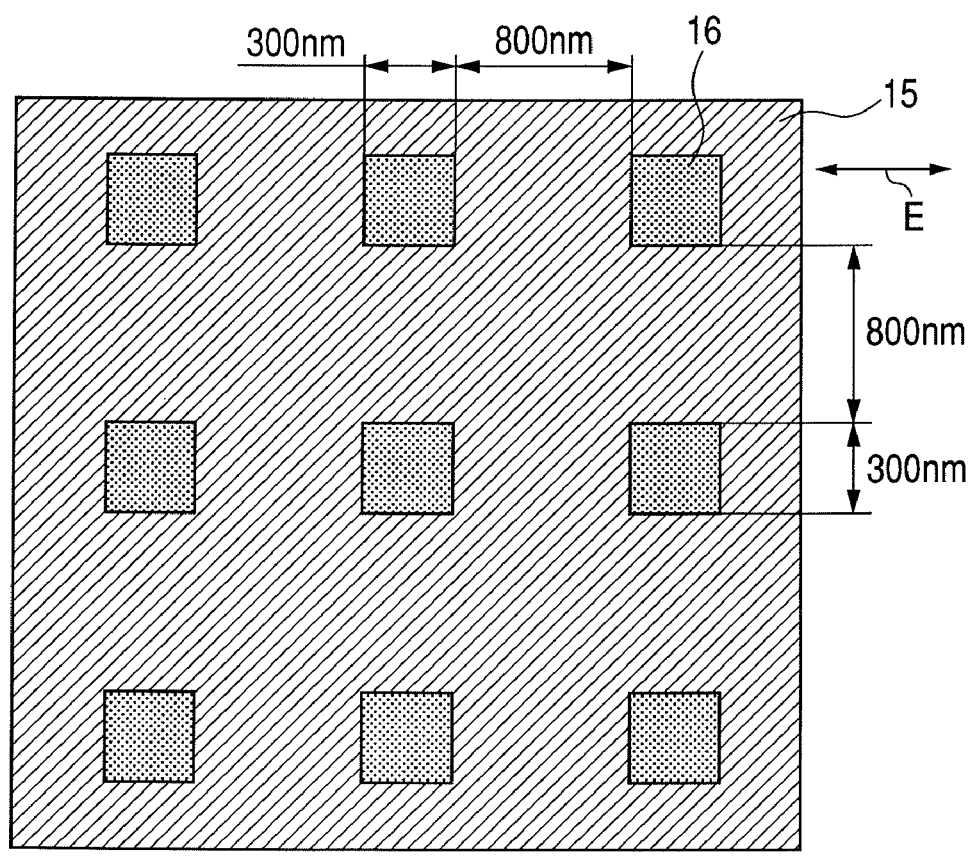
Figure 15A:
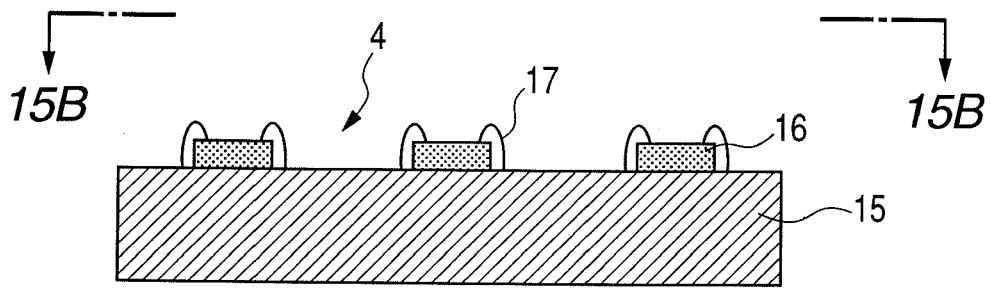
FIGS. 15A, 15B and 15C are schematic diagrams of the optical element in a state in which the resist layer is formed and a concavo-convex portion is formed.
Figure 15B:
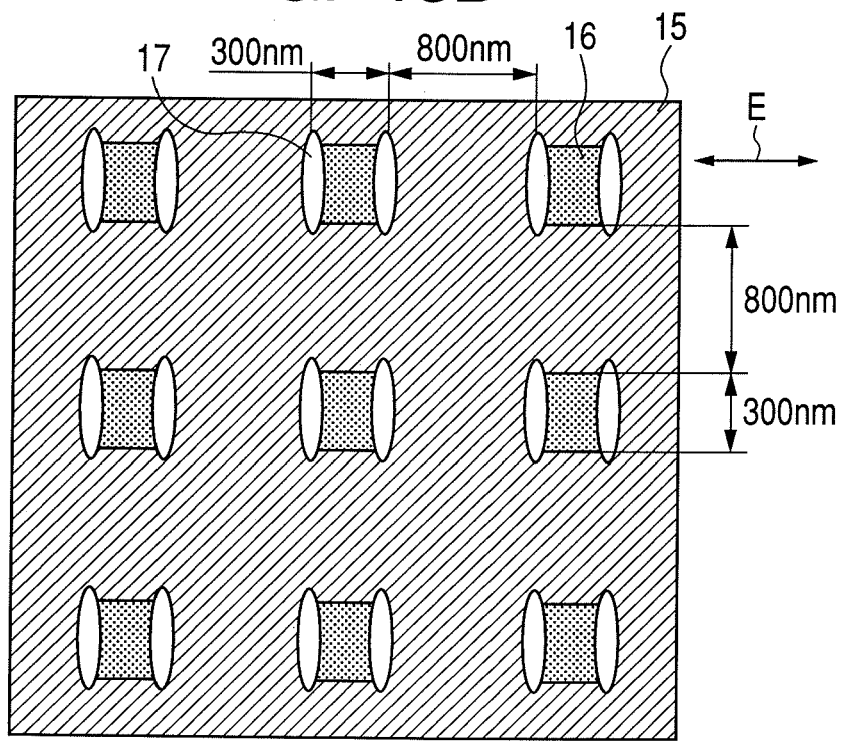
Figure 16A:
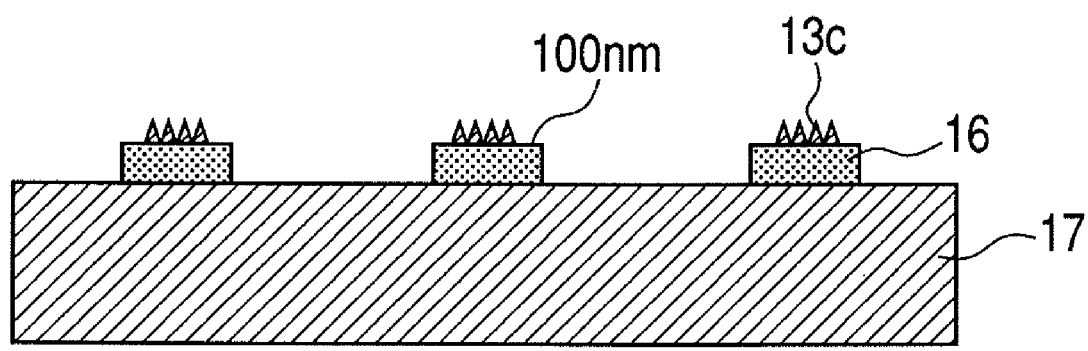
FIGS. 16A and 16B are schematic diagrams of the optical element in a state in which the resist layer is removed and the surface is decorated by the antibody.
Figure 16B:
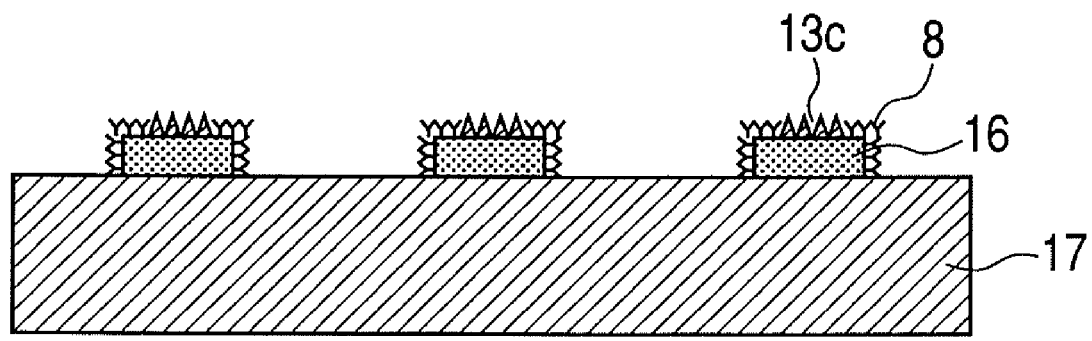

In FIGS. 14A and 14B are illustrated a schematic diagram of an optical element of the present embodiment at the preliminary stage of forming a dielectric layer. Further, in FIG. 15A is illustrated a state of forming a resist layer, in FIG. 15B is illustrated a state of forming a concavo-convex portion, in FIG. 16A is illustrated a state of removing the resist layer, and in FIG. 16B is illustrated a schematic diagram of an optical element in a state of decorating the surface by an antibody, respectively. Hereinafter, the manufacturing method of the optical element of the present embodiment will be described.

First, a conductive layer is formed on a support 15 serving as a substrate. The conductive layer is prepared in advance, which is formed into a square shape of 300 nm on a side as illustrated in FIG. 14B, and is disposed in a square lattice shape spaced at the intervals of approximately 800 nm.

The support 15 is a quartz substrate of approximately 525 μm in thickness, and a conductive fine particle 16 on the support 15 is an Au thin film of approximately 20 nm in thickness. However, the thickness of the conductive fine particle 16 is not limited to this. In the present embodiment, the material of the conductive fine particle 16 is not exclusively limited to Au, but a material capable of generating Plasmon resonance is preferable. The material of the conductive fine particle 16 in the present embodiment is preferably a metal having little dielectric loss particularly such as silver, copper, platinum, and aluminum, and other conductive substance such as a semiconductor may be also preferable. Further, the support 15 is not limited to quartz, but a substance high in transmissivity for the wavelength band for measuring the optical spectrum is preferable. The thickness of the support 15 also is not limited to this.

Next, by using a photolithography, a resist pattern is formed. After having coated a negative type photoresist, an exposure light is irradiated and a patterning is performed. At this time, an exposure is made in an exposure time in which a strong electric field area only in the vicinity of the conductive fine particle 16 is exposed so as to form a a latent image. This latent image is developed, thereby to form a patterned resist layer 17 (FIGS. 15A and 15B).

Figure 15C:
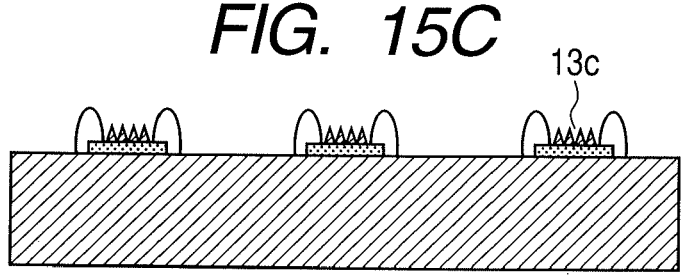

Next, this optical element is exposed to Ar gas plasma for a short period of time, thereby to form a concavo-convex portion 13c (FIG. 15C). However, here, the plasma is not limited to Argon, but may be a plasma if roughening the surface of the conductive fine particle 16.

At this time, the measuring light for this optical element 4 is a linearly polarized light, and has a polarized surface (in the direction to an arrow E) illustrated in FIG. 15B.

Next, the surface of the conductive fine particle 16 is modified by the antibody.

First, by using acetone and the like, the resist layer 17 only is put into a separated state (FIG. 16A). At this time, the concavo-convex portion 13c is disposed approximately 100 nm inside from the end face of the conductive fine particle 16.

For example, an anti-AFP (α-fetoprotein) antibody is immobilized with the Au surface of the conductive fine particle 16 as an antibody. In this case, the ethanol solution of 11-Mercaptoundecanoic acid having a thiol group is dripped by a spotter and the like, so that a carbolic group is exposed on the particle surface. Here, N-Hydroxysulfosuccinimide aqueous solution and 1-Ethyl-3-[3-dimenthylamino]proplyl carbodiimide hydrochloride aqueous solution are similarly dripped into the reaction area by the spotter and the like. As a result, a succinimide group is exposed on the fine particle surface. Here, streptoamidin is reacted, so as to modify the fine particle surface by streptoamidin. This fine particle is immobilized with the anti-AFP antibody biotinized. As a result, the conductive fine particle 16 is put into a state modified by the antibody 8 similarly to FIG. 16B.

Next, the antigen-antibody reaction and the optical spectrum measurement of a conductive microstructure element 55c formed with the concavo-convex portion 13c as described above will be described.

The antigen-antibody reaction and the optical spectrum measurement are performed by the configuration using a measurement substrate 57 as illustrated in the schematic diagram 17A.

First, the specimen including the AFP is injected from an injection port 52, and at the reaction well 53, the AFP is trapped on the conductive microstructure element 55c. After that, a specimen is discharged from a discharge port 54, and a phosphate buffer solution is injected from the injection port 52, and the interior of the reaction well 53 is cleansed. Finally, the phosphate buffer solution is filled.

Next, the optical spectrum of the conductive microstructure element 55c, the light from the light source 51 is introduced to the conductive microstructure element 55c and a scattered light from the conductive microstructure element 55c is measured by the spectroscopic measuring device 56.

Figure 17A:
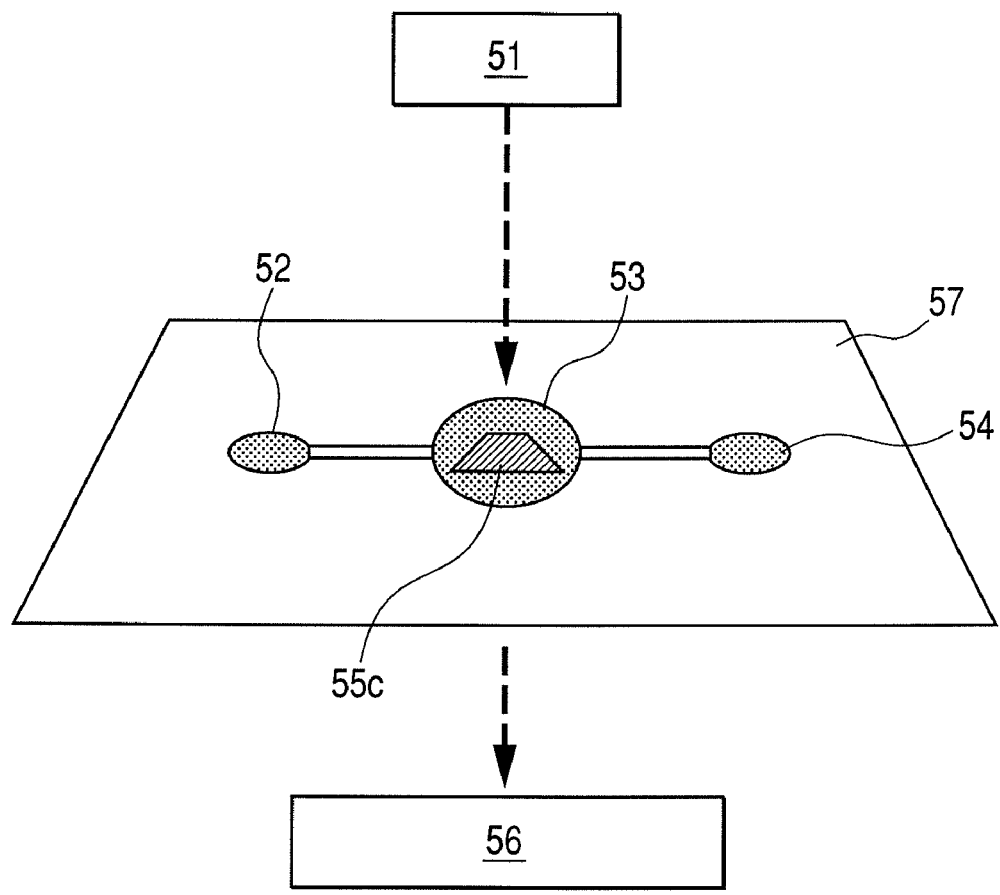
FIGS. 17A and 17B are a schematic diagram of the device performing the measurement of the antigen-antibody reaction and the optical spectrum, and a graph illustrating the measurement result of the optical spectrum.
Figure 17B:
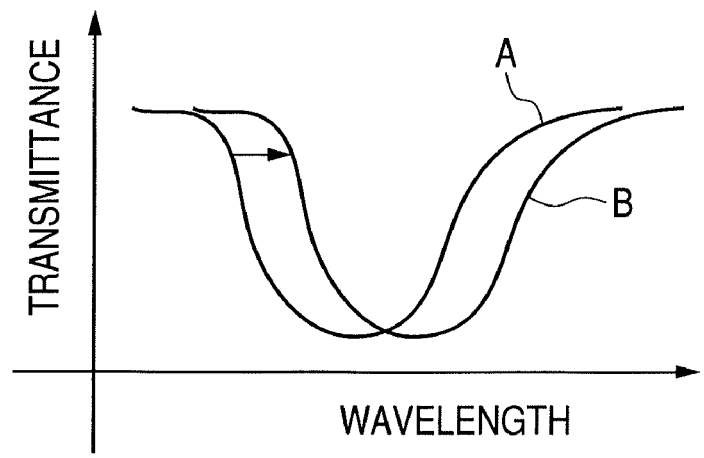

The optical spectrum is compared with the optical spectrum A before the reaction of the antigen antibody and the optical spectrum B after the reaction (FIG. 17B), the shift amount of the peak by the localized Plasmon resonance is determined, and from this shift amount, the density of the target substance is detected.

At this time, by using the AFP solution whose density is known in advance, the relationship between the signal value and the density is determined, so that the density of the measured specimen can be determined.

The optical element of the present invention is configured to form the concavo-convex portion 13c on the surface of the conductive microstructure and limit the region bound with the antigen. As a result, the fluctuation of the shift amount due to the difference in the bound region is suppressed, and a wide spreading of the observed optical spectrum after the reaction is suppressed. Hence, according to the optical element of the present invention, highly accurate density measurement can be performed.

In the present embodiment, while the structure of the conductive fine particle has been taken as a rectangular thin film, it is not limited to this, but may be a structure inducing the LSPR. Further, the light source for irradiating is not limited to the linearly polarized light, but may be a partially polarized light or non-polarized light.

Fourth Embodiment

Figure 18:
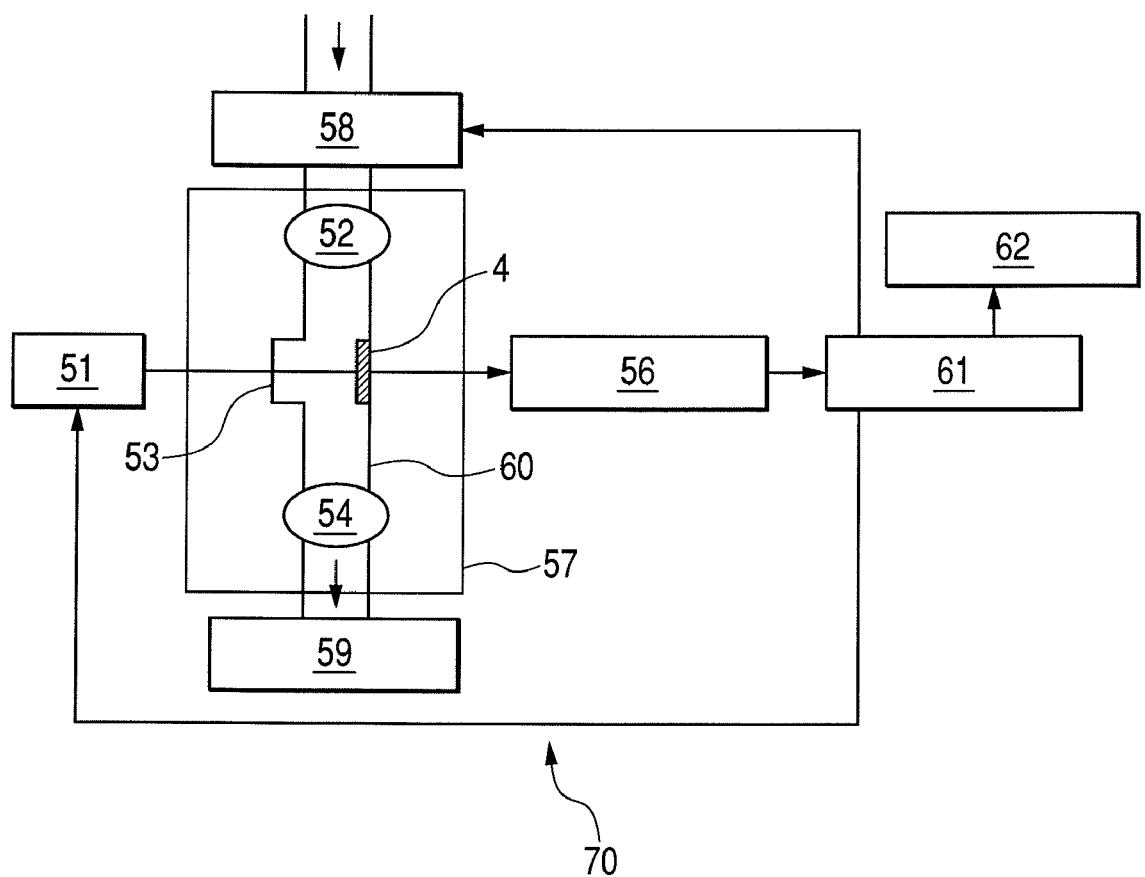
FIG. 18 is a constitutional example of a sensor device using the optical element of the present invention.
Figure 19A:
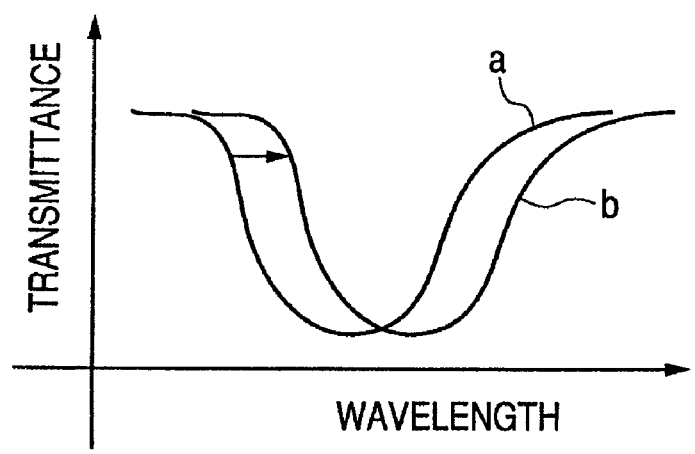
FIGS. 19A and 19B are a graph illustrating one example of the optical spectrum detected by a conventional measurement element and a schematic diagram of the conventional measurement element.
Figure 19B:
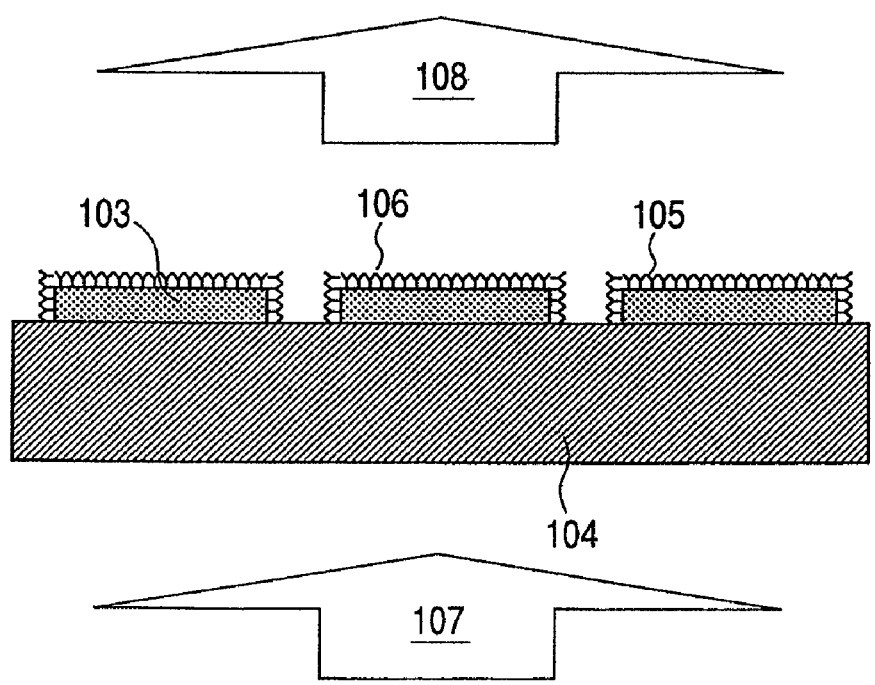

In FIG. 18 is illustrated a schematic diagram of a sensor device using an optical element of the present invention.

A sensor device 70 includes an optical system including a flow path 60, a light source 51, and a spectroscopic measuring device 56, and a measurement processing system including a central processing unit 61 and a display unit 62.

The flow path 60 includes a liquid feed pump 58, an injection port 52, a reaction well 53, a discharge port 54, and a waste liquid reservoir 59.

A reference liquid and a specimen liquid are fed to the injection port 52 from the liquid feed pump 58. The reference liquid and the specimen liquid flow into the reaction well 53 disposed with the optical element 4. The reference liquid and the specimen liquid flow while contacting the optical element inside the reaction well 53, and after having passed through the reaction well 53, are discharged from the discharge port 54 to the waste liquid reservoir 59.

The light source 51 irradiates a light to the optical element 4 inside the reaction well 53. Although the light source 51 is applicable with a tungsten lamp, it is not limited to this, but may be a light source having an emission wavelength in the measurement wavelength region. The spectroscopic measuring device 56 serving as an optical detection unit subjects a transmitted light transmitting the optical element 4 to spectrometry.

The data obtained by the spectroscopic measuring device 56 is processed at a central processing unit 61, and the processed result is displayed on a display unit 62 as a measurement result. The central processing unit 61 performs data processing, and at the same time, generates a control signal of the light source 51.

By configuring a sensing device using the optical element 4 of the present invention including the dielectric layer 13, the chemically modified portion 13b, or the concavo-convex portion 13c, highly accurate sensing (for example, a diffractive index sensing or biosensing) can be performed.

Fifth Embodiment

<1. Target Substance Detection Element>

FIGS. 27A, 27B, 27C, 27D, 27E, 27F and 27G are process drawings for explaining the manufacturing method of a detection element of the present invention.

A support 1004 uses a quartz wafer of 525 µm in thickness. The materials of an upper dielectric layer 1001 and a lower dielectric layer 1003 of a structure 1007 use $SiO_2$, and the material of a metal layer 1002 uses Au. Further, between the upper dielectric layer 1001 and the metal layer 1002, and between the metal layer 1002 and the lower dielectric layer 1003, Ti is under-coated as an adhesion layer (not illustrated). The shape of the structure 1007 seen from a plane xy is taken as a square shape of 150 nm on a side. The thickness of the upper dielectric layer 1001 and the lower dielectric layer 1003 is taken as 50 nm, respectively, and the thickness of the metal layer 1002 is also taken as 50 nm.

The manufacturing method of the detection element of the above described configuration will be described below.

Figure 27A:
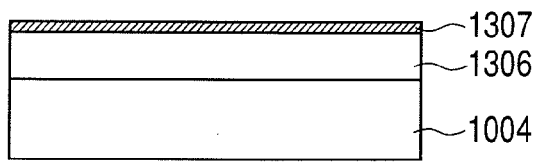
FIGS. 27A, 27B, 27C, 27D, 27E, 27F and 27G are process drawings illustrating one example of the manufacturing process of the detection element of the present invention.

First, a positive type resist (ZEP520A) is spin-coated on the support 1004 including a quart substrate, thereby to provide a resist layer 1306. Next, Espacer (made by Showa Denko K.K.) is spin-coated as a conductive polymer layer 1307 (FIG. 27A).

Figure 27B:
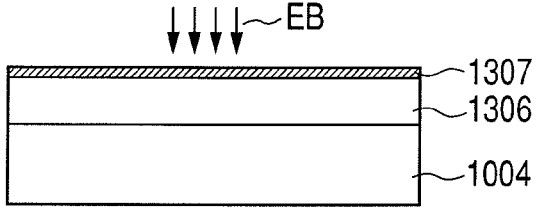

This is introduced into a chamber of an electron beam drawing device, and a desired pattern is drawn (FIG. 27B).

Figure 27C:
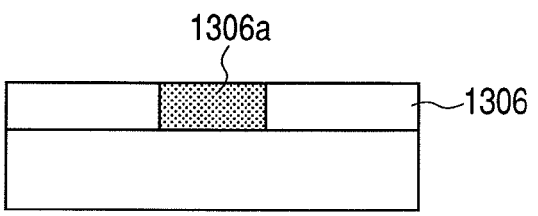

After having finished drawing, the pattern is cleansed by a pure water, and a conductive polymer layer is removed (FIG. 27C).

Figure 27D:
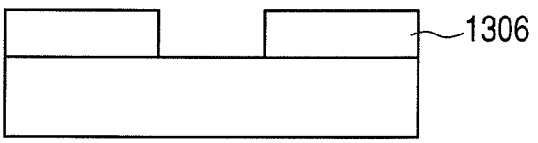

After that, it is developed by a developing solution, and the patterning of the resist layer 1306 is performed (FIG. 27D).

Figure 27E:
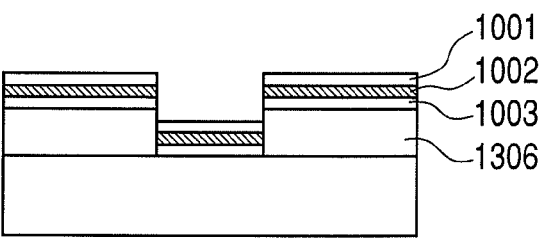

With the patterned resist layer 1306 taken as a mask, the lower dielectric layer 1003, the Ti adhering layer, the metal layer 1002, the Ti adhering layer, and the upper dielectric layer 1001 are deposited (FIG. 27E).

Figure 27F:
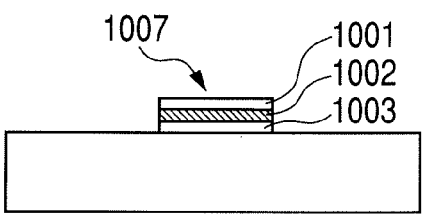

Next, a lift off is performed, and the lower dielectric layer 1003, the Ti adhering layer, the metal layer 1002, the Ti adhering layer, and the upper dielectric layer 1001 are removed except for the resist layer 1306 and the structure 1007 (FIG. 27F).

Figure 27G:
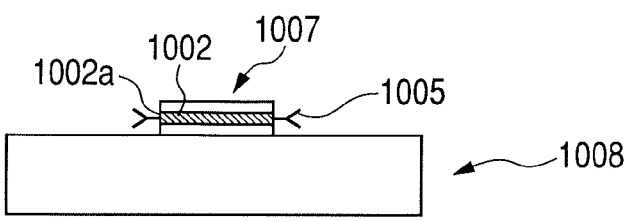

Finally, a capture 1005 is physically immobilized with the side face 1002a of the metal layer 1002, thereby to complete the detection element 1008 (FIG. 27G).

<2. Basic Optical Characteristic of Target Substance Detection Element>

A description will be made with reference to FIG. 28. FIG. 28 is a graph in which the transmissivity for the wavelength with the detection element 1008 including the structure 1007 as illustrated in FIGS. 20A and 20B and the detection element including the structure having no dielectric layer is calculated by an electromagnetic field simulation soft. In the figure, a bold line illustrates the transmissivity of the detection element 1008 illustrated in FIGS. 20A and 20B, and a thin line illustrates the transmissivity of the detection element having no dielectric layer. Further, together with each structure, transmission spectrums in the atmosphere and the pure water are illustrated.

The size of a laminated structure dot is x=y=150 nm. The thickness of the upper dielectric layer 1001 and the lower dielectric layer 1003 which are $SiO_{2\alpha}$, and the thickness of the metal layer 2 which is an Au layer are all 20 nm. Further, the size of Au dot is x=y=150 nm, and the thickness of the Au layer is 20 nm.

From the graph, it is appreciated that both in the atmosphere and in the pure water, the spectrum line width of the detection element having the structure 7 of the present invention is narrower than the spectrum line width of the detection element having the structure with no dielectric layer, and a Q value is improved.

<3. Target Substance Detection Kit/Device>

In the present embodiment, the measuring device illustrated in FIGS. 25A and 25B was used.

A light source 1202 has used a halogen lamp. An object lens 1203 has used a plane-convex cylinder lens (20 mm×40 mm, made by Sigma Koki Co. Ltd). A light receiving unit 1204 has used a multi-channel detector. A reaction well 1201 has used a processed PDMS substrate. Its surface is given a non-specific adsorption prevention treatment. Further, as a target substance detection element, a detection element 1080 of the present invention which is a Plasmon optical element is used.

<4. Measurement of Target Substance>

As the capture 1005, the detection element 1008 immobilized with an anti-IgE antibody is set inside the reaction well 1201, and the following protocol is performed.

(1) By a buffer solution adjusting pH, the reaction well 1201 and the detection element are given a good wash.

(2) A specimen liquid is injected 100 μL by a micro pipette, and is allowed to contact the detection element, thereby to initiate an antigen-antibody reaction.

(3) After allowing the specimen liquid to react for two hours, it is pulled out by the micro pipette, and the IgE antigen nonspecifically adsorbed is cleansed by the buffer solution.

(4) The buffer solution is injected again, and the measurement of the optical variation of the detection element which is a Plasmon optical element, that is, a spectrum measurement is performed.

Figure 24C:
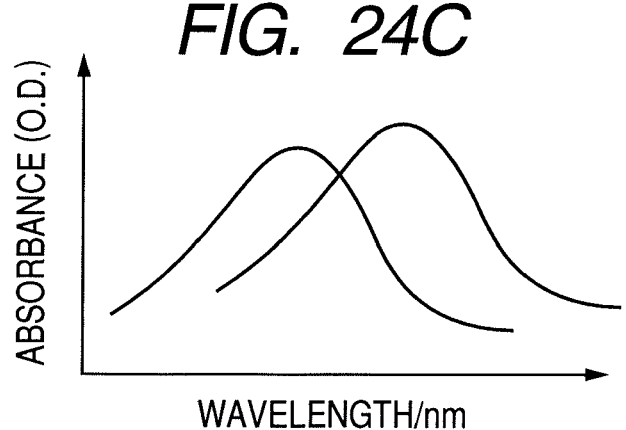
Figure 29:
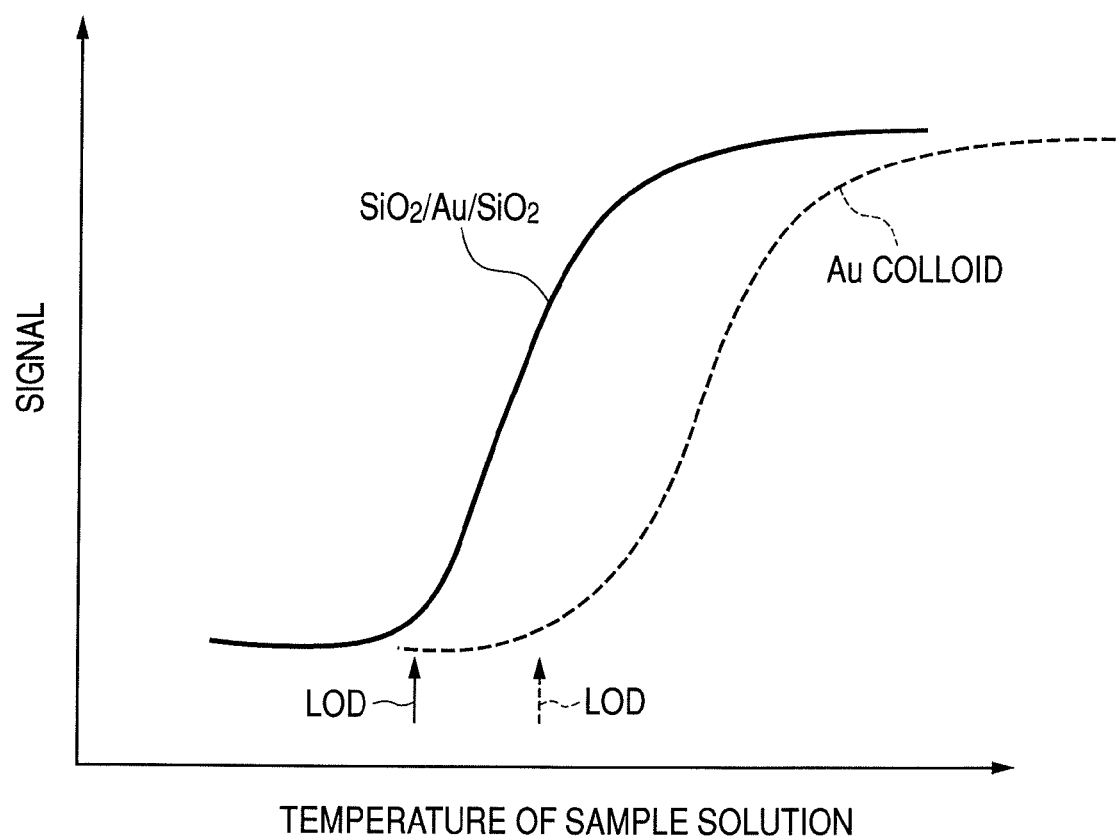
FIG. 29 is a graph illustrating an analytical curve with the detection element having the structure of the present invention and the detection element having the structure with no dielectric layer.

When the measurement is performed according to the above described protocol, a Plasmon resonance spectrum as illustrated in FIG. 24C is obtained. In the detection element of the configuration disclosed in the present invention, as compared with the detection element immobilized with a gold colloid and the detection element by the Au dot, the line width of the spectrum becomes thin. Further, according to the detection element of the present invention, since the capture 1005 is immobilized with the side face 1002a only, an amount of the capture 1005 is little, so that the detection element has much higher sensitivity. By analyzing this spectrum, an analytical curve as illustrated in FIG. 29 is obtained. A solid line indicates the analytical curve of the detection element of the present invention, whereas a broken line indicates the analytical line of the conventional detection element not limited in the region immobilized with the capture. By using the detection element of the present invention, it is possible to reduce a detection limit (LOD: Limit of detection) as compared with the conventional detection element.

Sixth Embodiment

<1. Target Substance Detection Element>

Figure 22A:
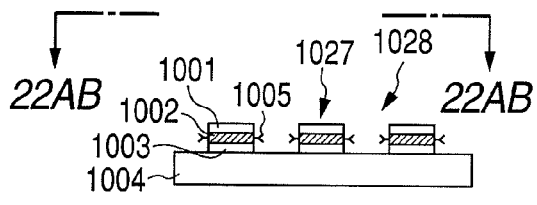
FIGS. 22AA, 22AB, 22BA, 22BB, 22CA and 22CB are side views and top plan views for explaining the outline of another example of the detection element of the present invention.
Figure 22B:
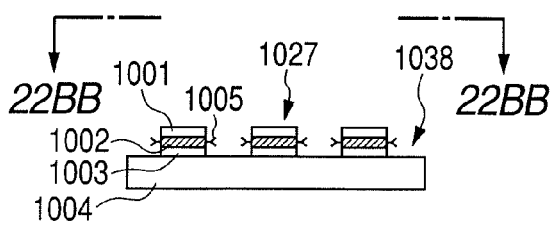
Figure 22A:
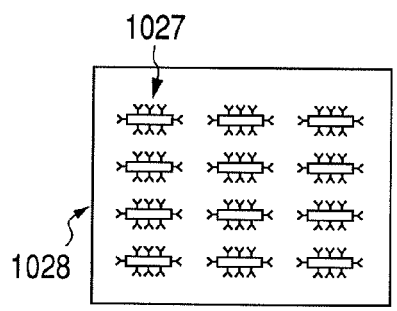
Figure 22B:
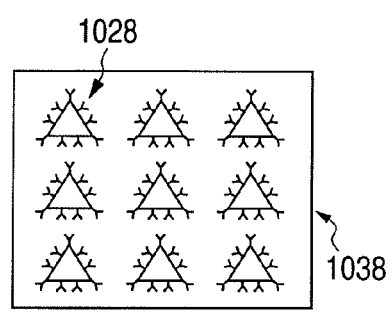
Figure 22C:
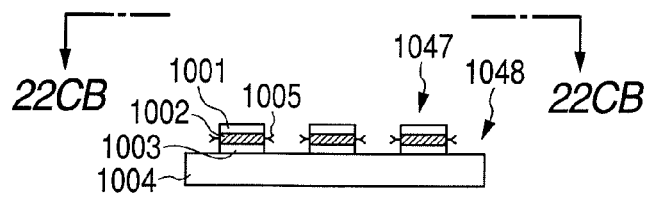
Figure 22C:
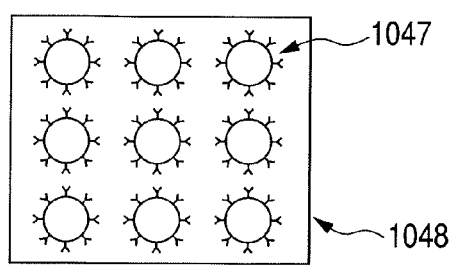
Figure 23A:
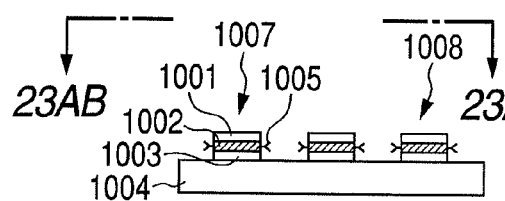
FIGS. 23AA, 23AB, 23BA, and 23BB are side views and top plan views for explaining the outline of another example of the detection element of the present invention.
Figure 23B:
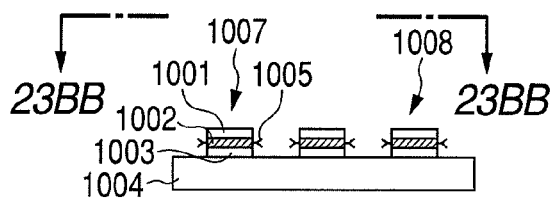
Figure 23A:
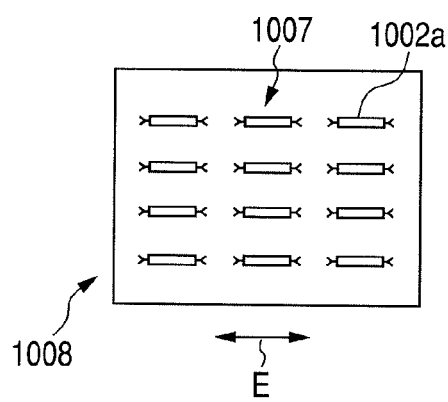
Figure 23B:
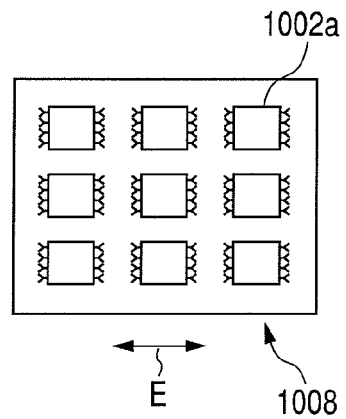
Figure 30A:
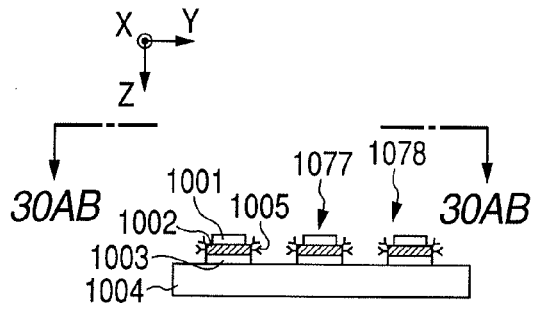
FIGS. 30AA, 30AB, 30BA, 30BB, 30CA and 30CB is side views and top plan views illustrating an example of the detection element having the structure including the dielectric layer of an area smaller than the area of a metal layer.

In the present embodiment, a detection element 1028 illustrated in FIGS. 22AA and 22AB and a detection element 1078 illustrated in FIGS. 30AA and 30AB were compared in sensitivity. An area of the plane xy of an upper electric layer 1001 of the detection element 1078 is made smaller than an area of the plane xy of a metal layer 1002. Hence, the detection element 1078 has not only a side face 1002a of the metal layer 1002 but also the upper face thereof immobilized with a capture 1005.

(First Element)

In the present embodiment, the detection element 1028 illustrated in FIGS. 22AA and 22AB which is immobilized with the capture 1005 only in the side face 1002a is taken as a first element.

A support 1004 of the first element has used a quart wafer of 525 μm in thickness. The materials of an upper dielectric layer 1001 and a lower dielectric layer 1003 of structure 1007 have used $SiO_2$, and the material of the metal layer 1002 has used Au. Further, between the upper dielectric layer 1001 and the metal layer 1002, and between the metal layer 1002 and the lower dielectric layer 1003, Ti is under-coated as an adhering layer (not illustrated).

The shape of the plane xy of the structure 1007 is a rectangle shape of 150 nm in major axis and 50 nm in minor axis.

(Second Element)

In the present embodiment, the detection element 1078 illustrated in FIGS. 30AA and 30AB which is immobilized with the capture 1005 not only with the side face 1002a but also on the upper surface portion is taken as a second element.

A support 1004 of the second element has used a quart wafer of 525 μm in thickness. The materials of an upper dielectric layer 1001 and a lower dielectric layer 1003 of structure 1007 have used $SiO_2$, and the material of the metal layer 1002 has used Au. Further, between the upper dielectric layer 1001 and the metal layer 1002, and between the metal layer 1002 and the lower dielectric layer 1003, Ti is undercoated as an adhering layer (not illustrated).

The shape of the plane xy of the metal layer 1002 and the lower dielectric layer 1003 is a rectangle shape of 150 nm in major axis and 50 nm in minor axis. The shape of the plane xy of the upper dielectric layer 1001 is a rectangular shape of 100 nm in major axis and 50 nm in minor axis.

<2. Target Substance Detection Kit/Device>

The measurement is performed by using the same kit/device used in the fifth embodiment.

<3. Measurement of Target Substance>

In the device of FIGS. 23AA, 23AB, 23BA AND 23BB, the detection element 1008 immobilized with an anti-IgE antibody is set to the device, and the following protocol is performed.

(1) By a buffer solution adjusting pH, the reaction well and the target substance detection element are given a good wash.

(2) A specimen liquid is injected 100 μL by a micro pipette, and is allowed to contact the detection element, thereby to initiate an antigen-antibody reaction.

(3) After allowing the specimen liquid to react for two hours, it is pulled out by the micro pipette, and a CRP antigen non specifically adsorbed is cleansed by the buffer solution.

(4) The buffer solution is injected again, and the measurement of the optical variation of the detection element which is the Plasmon optical element, that is, the spectrum measurement is performed.

When the measurement on each element is performed according to the above described protocol, the analytical curve as illustrated in FIG. 31 is obtained. In FIG. 31, a solid line indicates the analytical curve of the detection element 1008 including the first element, a thin line indicates an analytical curve of the detection element 1078 including the second element, and a broken line indicates an analytical line of the detection element using an Au colloid including no dielectric layer. As illustrated in the same figure, it is possible for both of the elements to make a detection limit (LOD: Limit of detection) smaller than the detection element using the Au colloid as conventionally disclosed. Further, the Plasmon element illustrated in FIGS. 22AA and 22AB is larger in area of the dielectric layer than the Plasmon element illustrated in FIGS. 30AA and 30AB, and becomes small in the line width of the spectrum, and therefore, the LOD value becomes smaller.

Figure 30B:
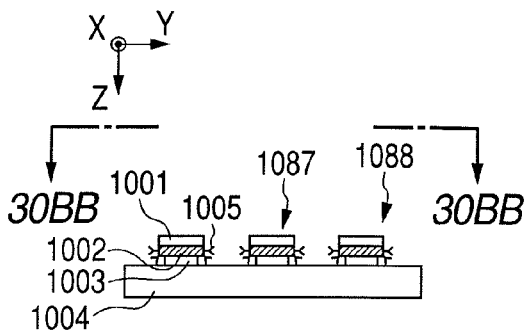
Figure 30A:
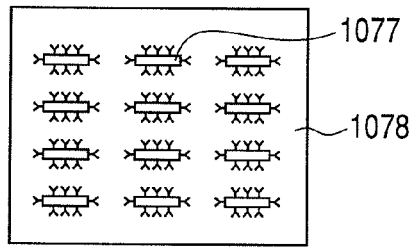
Figure 30B:
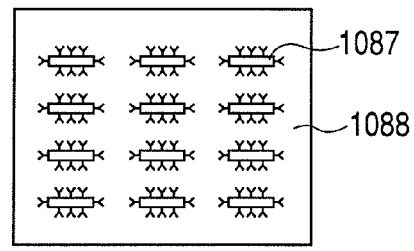
Figure 30C:
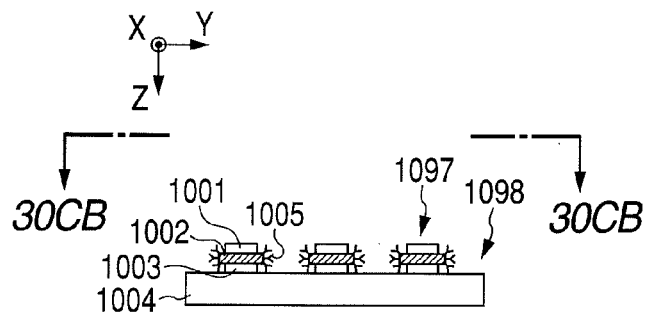
Figure 30C:
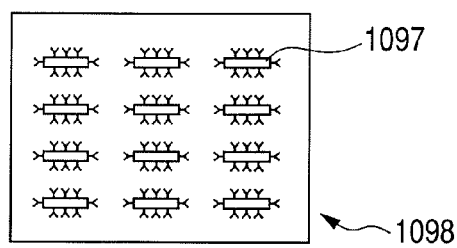

The element whose plane xy of the lower dielectric layer 1003 as illustrated in FIGS. 30BA and 30BB is smaller than the metal layer 1002, and the elements whose planes xy of the upper dielectric layer 1001 and the lower dielectric layer 1003 as illustrated in FIGS. 30CA and 30CB are smaller than the metal layer 1002, respectively have produced the same result. In FIGS. 30AA to 30CB, numerals 1078, 1088 and 1098 denote detection elements, and numerals 1077, 1087 and 1097 denotes structures. That is, the Plasmon element illustrated in FIGS. 22AA and 22AB is larger in area of the dielectric layer than the Plasmon elements illustrated in FIGS. 30BA, 30BB, 30CA and 30CB, and becomes narrower in line width of the spectrum, and therefore, has become small in the LOD value.

Seventh Embodiment

<1. Target Substance Detection Element>

With reference to FIGS. 27A to 27G, an element configuration for target substance detection according to the present embodiment will be described. A support 1304 uses a quart wafer of 525 μm in thickness. With respect to the material of a nano structure made of a metal and a dielectric, the materials of structures 1301 and 1303 use $SiO_2$, and the material of a structure 1302 uses gold. Further, between $SiO_2$ and Au, Ti is under-coated as an adhering layer (not illustrated).

The shape of the plane xy of the Plasmon element is taken as a square shape of 150 nm on a side. The thickness of the upper and lower dielectric layers is taken as 50 nm, respectively, and the thickness of the metal is also taken as 50 nm.

<2. Target Substance Detection Kit/Device>

The measuring device has used the device as illustrated in FIGS. 26A and 26B.

A light source 1601 has used a halogen lamp, and a light receiving unit 1602 has used a multi-channel detector (made by Hamamatsu Photonics, Japan). A specimen reservoir 1603 has used an Eppendorf tube, and a cleaning liquid reservoir 1604 has used a biochemical glass bottle. A flow path switching valve 1605 has used a three-way valve (made by GL science, Japan), and a liquid feeding unit 1606 has used a syringe pump (kd Scientific KDS200), and a waste liquid tank 1607 has used a syringe. Liquid feeding and waste liquid tubes 1608 and 1609 have used Teflon tubes. A flow path 1611 is formed on a cover (PDMS substrate) with a size of 1 mm in width, 100 μm in width, and 40 mm in length. A substrate 1613 has used a quart glass, and an object lens 1615 has used a plane-convex cylinder lens (20 nm×40 nm, made by Sigma Koki Co. Ltd).

The detection element has used a detection element 1008 illustrated in FIGS. 20A and 20B.

<3. Measurement of Target Substance>

In the device of FIGS. 25A and 25B, the target substance detection element 1610 immobilized with an anti-CRP antibody is set to the device, and the following protocol is performed.

(1) The three-way valve 1605 is switched over to the cleaning liquid reservoir 1604 side, and a buffer solution adjusting pH to 7.4 is let flow for ten minutes at a flow rate of 0.1 (ml/min.), and the detection element 1008 is given a good wash.

(2) The three-way valve 1605 is switched over to the cleaning liquid reservoir 1603 side, and a specimen is let flow for ten minutes at a flow rate of 0.1 (ml/min.), thereby to initiate an antigen-antibody reaction.

(3) While the liquid is let flow over the specimen, a reflection spectrum is measured every definite period time.

(4) The three-way valve 1605 is switched over again to the cleaning liquid reservoir 1604 side, and a buffer solution is let flow for ten minutes at a flow rate 0.1 (ml/min.), and the antigen nonspecifically adsorbed is washed away.

By the above described protocol, the spectrum illustrated in FIG. 24C is obtained at each reaction time.

Figure 32:
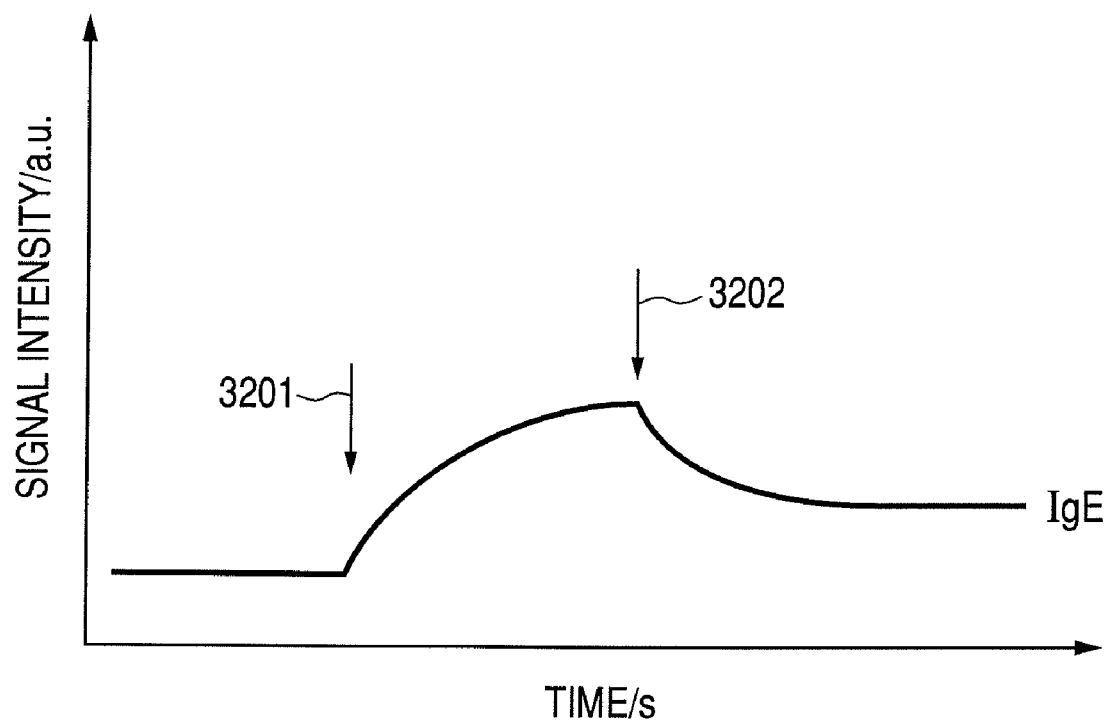
FIG. 32 is a time course of the antigen-antibody reaction in the detection element of the present invention.

This spectrum is subjected to an exponential fitting by a graph soft, thereby to determine a peak value of the spectrum, so that a time course of the antigen-antibody reaction is obtained as illustrated by FIG. 32. In the same figure, an arrow 3201 indicates a liquid injection starting point of time, and an arrow 3202 indicates a cleaning starting point of time.

Eighth Embodiment

<1. Target Substance Detection Element>

In the present embodiment, a time course of each antigen-antibody reaction of an anti-CRP antibody, an anti-IgG antibody, an anti IgM antibody, and an anti IgA antibody by the detection element 1008 manufactured by the manufacturing process illustrated in FIGS. 27A, 27B, 27C, 27D, 27E, 27F and 27G has been determined.

A support 1004 has used a quart wafer of 525 µm in thickness. The materials of an upper dielectric layer 1001 and a lower dielectric layer 1003 of structure 1007 have used $SiO_2$, and the material of a metal layer 1002 has used Au. Further, between the upper dielectric layer 1001 and the metal layer 1002, and between the metal layer 1002 and the lower dielectric layer 1003, Ti is under-coated as an adhering layer (not illustrated).

A capture 1005 uses the anti-CRP antibody, the anti-IgG antibody, the anti IgM antibody, and the anti IgA antibody.

The structure 1007 is in the square shape illustrated in FIGS. 20A and 20B, and is 150 nm on a side. Each thickness of the upper dielectric layer 1001, the metal layer 1002, and the lower dielectric layer 1003 is 50 nm.

<2. Target Substance Measuring Device>

Figure 33:
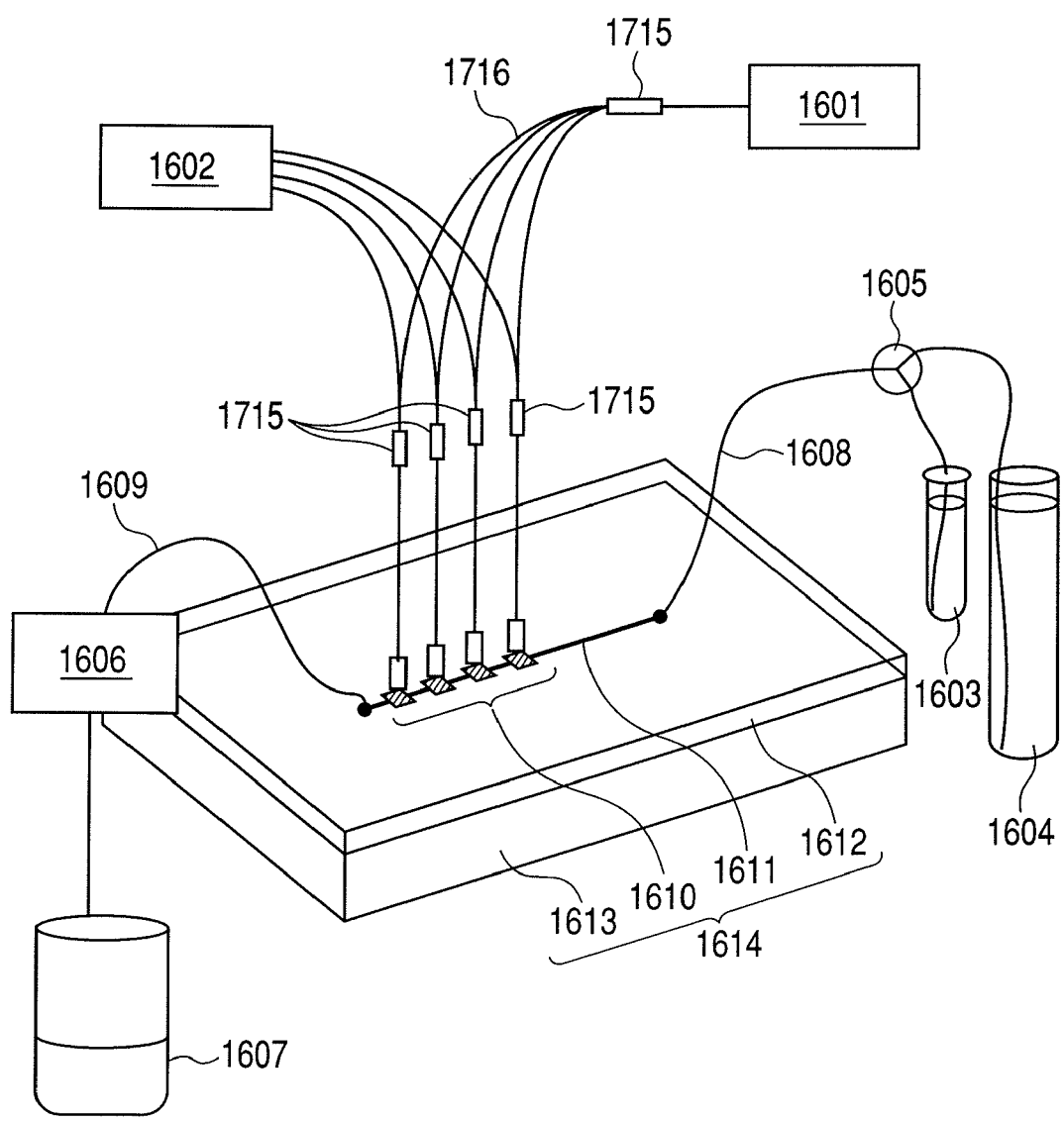
FIG. 33 is a schematic diagram of one example of the measuring device using a multi-channel detector capable of simultaneously measuring four channels including the detection element of the present invention.

In the present embodiment, the measuring device illustrated in FIG. 33 has been used.

The measuring device used in the present embodiment is made of an optical measuring system and a liquid flow path system.

Although the optical measuring system of the present embodiment is different from the measuring device illustrated in FIGS. 26A and 26B in using a multi-channel detector capable of simultaneously measuring 4 channels, it is basically the same otherwise.

The optical measuring system includes a light source 1601, a light receiving unit 1602, and an optical fiber 1716. The optical fiber 1716 connected to the light source 1601 and the optical fiber 1716 connected to a spectroscope 1602 are connected by a coupler 1715. If the optical fiber 1716 can sufficiently take a light quantity from the light source at each wavelength band, no particular limit is imposed. Here, a fiber of visible wavelength band is preferably used.

<3. Measurement of Target Substance>

The detection elements 1008 immobilized with the anti-CRP antibody, the anti-IgG antibody, the anti-IgM antibody, and the anti-IgA antibody as the capture 1005 are prepared, respectively, and each detection element 1008 is set to the measuring device illustrated in FIG. 33, and the following protocol is performed.

(1) A three-way valve 1605 is switched over to the cleaning liquid reservoir 1604 side, and a buffer solution adjusting pH to 7.4 is let flow for ten minutes at a flow rate of 0.1 (ml/min.), so that the detection element 1008 is given a good wash.

(2) The three-way valve 1605 is switched over to the cleaning liquid reservoir 1603 side, and the specimen is let flow for ten minutes at a flow rate of 0.1 (ml/min.), thereby to initiate an antigen-antibody reaction.

(3) The three-way valve 1605 is switched over again to the cleaning liquid reservoir 1604 side, and the buffer solution is let flow for ten minutes at a flow rate of 0.1 (ml/min.), and the antigen nonspecifically adsorbed is washed away.

Figure 34:
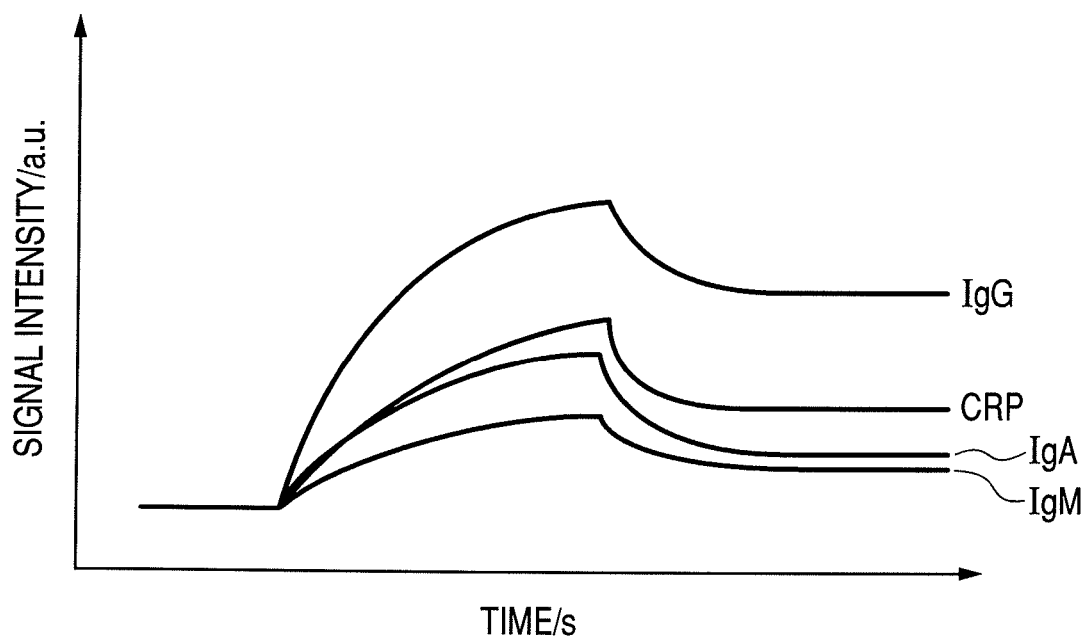
FIG. 34 is a time course of the antigen-antibody reaction in the detection element of the present invention.

By the above described protocol, the spectrum illustrated in FIG. 24C is obtained for every reaction field. This spectrum is subjected to an exponential fitting by a graph soft, thereby to determine a peak value of the spectrum, so that, as illustrated in FIG. 34, kinetics measurement of the reaction is made possible for every marker protein. By measuring a plurality of disease marker proteins and reaction profiles of the antibodies as described above, it is possible to check the cause of the disease at high accuracy by the measurement of one protein.

The optical element according to the embodiment of the present invention as described above is configured such that the binding capacity of the measured molecule on the surface of the structure is distributed in the direction to the electric displacement vector generated inside the structure. As a result, the fluctuation of the shift amount due to the difference of the binding region of the measured molecule can be suppressed, and the wide spreading of the observed optical spectrum after the reaction can be suppressed, thereby enabling a highly accurate density measurement.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Applications No. 2007-070597, filed Mar. 19, 2007, and No. 2007-070598, filed Mar. 19, 2007 which are hereby incorporated by reference herein in their entirety.

What is claimed is:

1. An optical element for detecting an optical spectrum shift based on binding of measuring molecules to the optical element by utilizing localized plasmon resonance, the optical element comprising:
   a substrate; and
   a conductive member that gives rise to a localized plasmon by irradiation of light, the conductive member being provided on the substrate,
   wherein a surface condition of the conductive member is different in a direction parallel to an electric field of the irradiated light between (a) a part adjacent to an edge of the conductive member and (b) another part of the conductive member, by surface processing to the another part such that the measuring molecules bind selectively to the part adjacent to the edge of the conductive member.

2. The optical element according to claim 1, wherein the width of the part adjacent to the edge is 100 nm.

3. The optical element according to claim 1, wherein the another part is covered by a dielectric for suppressing the binding of the measuring molecules.

4. The optical element according to claim 1, wherein the another part is chemically modified for suppressing the binding of the measuring molecules.

5. The optical element according to claim 1, wherein the another part is roughened for suppressing the binding of the measuring molecules.

6. The optical element according to claim 1, wherein the conductive member is metal.

7. The optical element according to claim 1, wherein the material of the conductive member includes a substance selected from the group consisting of gold, silver, platinum, and aluminum.

8. A sensor device, comprising:
   a light source,
   the optical element according to claim 1,
   a reaction well in which the optical element is disposed and in which a measured substance including the measuring molecules passes through by contacting the optical element, and
   an optical detection unit for detecting a transmitted light of the light irradiated on the optical element from the light source.

* * * * *